US008452022B2

(12) United States Patent
Asada

(10) Patent No.: US 8,452,022 B2
(45) Date of Patent: May 28, 2013

(54) DIGITAL FILTER CIRCUIT, DIGITAL FILTER PROGRAM AND NOISE CANCELING SYSTEM

(75) Inventor: Kohei Asada, Kanagawa (JP)

(73) Assignee: Sony Corporation, Tokyo (JP)

(*) Notice: Subject to any disclaimer, the term of this patent is extended or adjusted under 35 U.S.C. 154(b) by 1381 days.

(21) Appl. No.: 11/875,374

(22) Filed: Oct. 19, 2007

(65) Prior Publication Data

US 2008/0107282 A1 May 8, 2008

(30) Foreign Application Priority Data

Nov. 7, 2006 (JP) ................................ 2006-301211

(51) Int. Cl.

| | |
|---|---|
| ***A61F 11/06*** | (2006.01) |
| ***H04B 15/00*** | (2006.01) |
| ***H03B 29/00*** | (2006.01) |
| ***H03M 3/00*** | (2006.01) |
| ***H03M 7/00*** | (2006.01) |

(52) U.S. Cl.

USPC ... 381/71.14; 381/71.1; 381/71.6; 381/71.11; 381/71.12; 381/72; 381/94.8; 341/61; 341/143

(58) Field of Classification Search

USPC .......... 381/71.14, 71.6, 94.8, 72, 71.1, 71.11, 381/71.12

See application file for complete search history.

(56) References Cited

U.S. PATENT DOCUMENTS

| | | | | |
|---|---|---|---|---|
| 4,654,871 | A * | 3/1987 | Chaplin et al. | 381/72 |
| 5,276,740 | A | 1/1994 | Inanaga et al. | |
| 6,058,194 | A * | 5/2000 | Gulli et al. | 381/94.8 |
| 6,898,293 | B2 * | 5/2005 | Kaulberg | 381/318 |
| 7,110,554 | B2 * | 9/2006 | Brennan et al. | 381/94.7 |
| 7,756,592 | B2 * | 7/2010 | Craven | 700/30 |
| 7,885,417 | B2 * | 2/2011 | Christoph | 381/71.11 |
| 2003/0026438 | A1 * | 2/2003 | Ray et al. | 381/71.11 |
| 2004/0059764 | A1 * | 3/2004 | Takeda | 708/313 |
| 2008/0112569 | A1 | 5/2008 | Asada | |
| 2008/0112570 | A1 * | 5/2008 | Asada et al. | 381/71.6 |
| 2008/0152169 | A1 | 6/2008 | Asada et al. | |
| 2008/0159555 | A1 | 7/2008 | Asada et al. | |

(Continued)

FOREIGN PATENT DOCUMENTS

| | | | |
|---|---|---|---|
| CN | 1494211 | A | 5/2004 |
| JP | 3-96199 | | 4/1991 |

(Continued)

OTHER PUBLICATIONS

Japanese Office Action issued Dec. 27, 2011, in Patent Application No. 2006-301211.

(Continued)

*Primary Examiner* — David Warren
*Assistant Examiner* — Christina Russell
(74) *Attorney, Agent, or Firm* — Oblon, Spivak, McClelland, Maier & Neustadt, L.L.P.

(57) ABSTRACT

Disclosed herein is a digital filter circuit for producing a noise reduction signal for reducing noise based on a noise signal outputted from a microphone which collects the noise, including: an analog/digital conversion section; a first digital filter section; an arithmetic operation processing section; a second digital filter section; and a digital/analog conversion section. The first digital filter section and/or the second digital filter section are configured such that a predetermined attenuation amount is obtained within a predetermined range in the proximity of a sampling frequency around the sampling frequency.

14 Claims, 24 Drawing Sheets

U.S. PATENT DOCUMENTS

| | | | | |
|---|---|---|---|---|
| 2008/0159568 | A1 | 7/2008 | Asada et al. | |
| 2008/0170725 | A1 | 7/2008 | Asada et al. | |
| 2008/0186218 | A1 | 8/2008 | Ohkuri et al. | |
| 2008/0187148 | A1 | 8/2008 | Itabashi et al. | |
| 2008/0212791 | A1 | 9/2008 | Asada et al. | |
| 2008/0310645 | A1* | 12/2008 | Itabashi et al. | 381/71.6 |

FOREIGN PATENT DOCUMENTS

| | | |
|---|---|---|
| JP | 3-214892 | 9/1991 |
| JP | 8-18399 | 1/1996 |
| JP | 9-195791 | 7/1997 |
| JP | 2000-59876 | 2/2000 |

OTHER PUBLICATIONS

Office Action dated Oct. 25, 2010 in Chinese Patent Application No. 200710169803.X (with English-language Translation).

Office Action dated Mar. 31, 2011 in Chinese Patent Application No. 200710169803.X (with English-language Translation).

Office Action dated Oct. 30, 2012 in Japanese Patent Application No. 2006-301211 filed Nov. 7, 2006.

Huang Baohua, "A Sample Point Sequence Delayer Based on Interpolation and Decimation Technology", Military Telecommunications Technology, Dec. 31, 1998 (with English-language Translation for Relevant Parts).

* cited by examiner $$P = \frac{1}{1 + ADHM\beta} N + \frac{AHD}{1 + ADHM\beta} ES \quad \ldots(1)$$

$$\left| \frac{1}{1 + ADHM\beta} \right| < 1 \quad \ldots(2)$$

$$E = (1 + ADHM\beta) \quad \ldots(3)$$

$$P = \frac{1}{1 + ADHM\beta} N + ADHS \quad \ldots(4)$$

FIG. 5
$$P = -F'ADHM\alpha N + FN + ADHS \quad \ldots(1)$$
$$F = F'ADHM\alpha N \quad \ldots(2)$$
$$P = ADHS \quad \ldots(3)$$
FIG. 6A
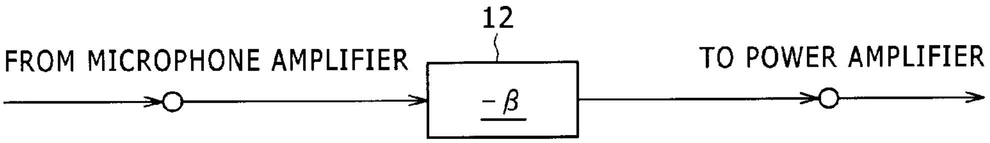
FIG. 6B
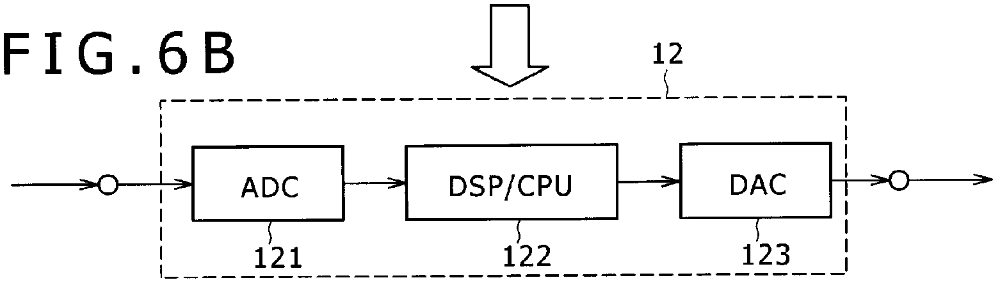
FIG. 6C
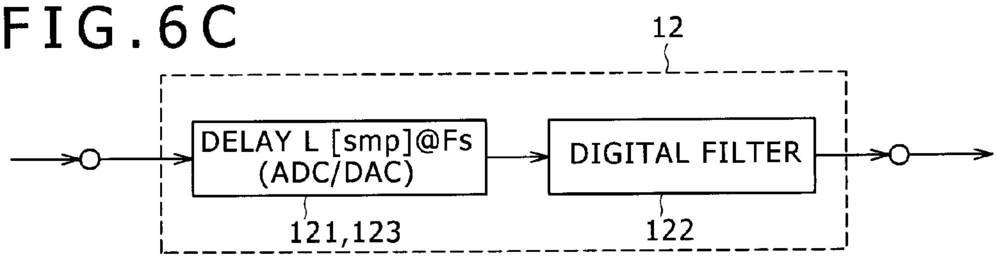

FIG. 20

| | (A) ENVIRONMENTAL NOISE | (B) HEADPHONE PASSIVE SOUND INSULATION | (C) MICROPHONE & AMPLIFIER | (D) ADC OF Σ-Δ bit TYPE HAVING BUILT-IN LOW-ORDER FIR |
|---|---|---|---|---|
| 500Hz | (ACCORDING TO 1/F CHARACTERISTIC) FREQUENCY BAND NOISE AND NEIGHBORHOOD NOISE EXHIBIT APPROXIMATELY -20db AT 5kHz AND AROUND 500Hz, RESPECTIVELY | SOUND INSULATION EFFECT IS LOW | NORMALLY, SUBSTANTIALLY EQUAL FOR 500Hz, 5kHz | IF 95.5kHz, 96.5kHz, ... EXIST, THEY HAVE INFLUENCE ON COMPONENTS OF 5kHz |
| 5kHz | | SOUND IS INSULATED MUCH | ATTENUATED IN FREQUENCIES HIGHER THAN 20kHz | IF 91kHz, 101kHz, ... EXIST, THEY HAVE INFLUENCE ON COMPONENTS OF 5kHz |
| RE-MARKS | USUALLY, DISAGREEABLE LOW FREQUENCY REGION NOISE IS REDUCTION OBJECT | IN CLOSED TYPE, HIGH FREQUENCY REGION SOUND INSULATION IS EASY | IT IS POSSIBLE TO ALSO DESIGN SO AS TO ATTENUATE IN HIGH FREQUENCY REGION | AS FILTER IS APPLIED, MORE ATTENUATION OCCURS IN IN HIGH FREQUENCY REGION |

| | (E) DSP/CPU | (F) ADC OF Σ-Δ bit TYPE HAVING BUILT-IN LOW-ORDER FIR | (G) HEADPHONE AMPLIFIER | (H) HEADPHONE DRIVER/ HOUSING INTERNAL SPACE |
|---|---|---|---|---|
| 500Hz | NORMALLY, FILTERING PROCESS OF HIGH FREQUENCY REGION ATTENUATION TYPE (INTERNAL SIGNAL PROCESS IS PERFORMED FOR 24 kHz OR LESS) | 95.5kHz, 96.5kHz, ... ARE GENERATED SIMULTANEOUSLY | NORMALLY, SUBSTANTIALLY EQUAL FOR 500Hz, 5kHz | NORMALLY SUBSTANTIALLY EQUAL |
| 5kHz | | 91kHz, 101kHz, ... ARE GENERATED SIMULTANEOUSLY | ATTENUATED IN FREQUENCIES HIGHER THAN 20kHz | |
| RE-MARKS | CALCULATE TOGETHER WITH COMPONENTS FOLDED BACK BY ADC | AS FILTER IS APPLIED, MORE ATTENUATION OCCURS IN IN HIGH FREQUENCY REGION | IT IS POSSIBLE TO ALSO DESIGN SO AS TO ATTENUATE IN HIGH FREQUENCY REGION | IT IS POSSIBLE TO ALSO DESIGN SO AS TO ATTENUATE IN HIGH FREQUENCY REGION |

FIG.22

| | (A) ENVIRONMENTAL NOISE | (B) HEADPHONE PASSIVE SOUND INSULATION | (C) MICROPHONE & AMPLIFIER | (D) ADC OF Σ-Δ bit TYPE HAVING BUILT-IN LOW-ORDER FIR |
|---|---|---|---|---|
| 500Hz | (ACCORDING TO 1/F CHARACTERISTIC) FREQUENCY BAND NOISE AND NEIGHBORHOOD NOISE EXHIBIT APPROXIMATELY -20db AT 5kHz AND AROUND 500Hz, RESPECTIVELY | SOUND INSULATION EFFECT IS LOW | NORMALLY, SUBSTANTIALLY EQUAL FOR 500Hz, 5kHz | IF 47.5kHz, 48.5kHz, ... EXIST, THEY HAVE INFLUENCE ON COMPONENTS OF 5kHz |
| 5kHz | | SOUND IS INSULATED MUCH | ATTENUATED IN FREQUENCIES HIGHER THAN 20kHz | IF 43kHz, 53kHz, ... EXIST, THEY HAVE INFLUENCE ON COMPONENTS OF 5kHz |
| RE-MARKS | USUALLY, DISAGREEABLE LOW FREQUENCY REGION NOISE IS REDUCTION OBJECT | IN CLOSED TYPE, HIGH FREQUENCY REGION SOUND INSULATION IS EASY | IT IS POSSIBLE TO ALSO DESIGN SO AS TO ATTENUATE IN HIGH FREQUENCY REGION | AS FILTER IS APPLIED, MORE ATTENUATION OCCURS IN IN HIGH FREQUENCY REGION |

| | (E) DSP/CPU | (F) ADC OF Σ-Δ bit TYPE HAVING BUILT-IN LOW-ORDER FIR | (G) HEADPHONE AMPLIFIER | (H) HEADPHONE DRIVER/ HOUSING INTERNAL SPACE |
|---|---|---|---|---|
| 500Hz | NORMALLY, FILTERING PROCESS OF HIGH FREQUENCY REGION ATTENUATION TYPE (INTERNAL SIGNAL PROCESS IS PERFORMED FOR 24 kHz OR LESS) | 47.5kHz, 48.5kHz, ... ARE GENERATED SIMULTANEOUSLY | NORMALLY, SUBSTANTIALLY EQUAL FOR 500Hz, 5kHz | NORMALLY SUBSTANTIALLY EQUAL |
| 5kHz | | 43kHz, 53kHz, ... ARE GENERATED SIMULTANEOUSLY | ATTENUATED IN FREQUENCIES HIGHER THAN 20kHz | |
| RE-MARKS | CALCULATE TOGETHER WITH COMPONENTS FOLDED BACK BY ADC | AS FILTER IS APPLIED, MORE ATTENUATION OCCURS IN IN HIGH FREQUENCY REGION | IT IS POSSIBLE TO ALSO DESIGN SO AS TO ATTENUATE IN HIGH FREQUENCY REGION | IT IS POSSIBLE TO ALSO DESIGN SO AS TO ATTENUATE IN HIGH FREQUENCY REGION |

DIGITAL FILTER CIRCUIT, DIGITAL FILTER PROGRAM AND NOISE CANCELING SYSTEM

CROSS REFERENCES TO RELATED APPLICATIONS

The present invention contains subject matter related to Japanese Patent Application JP 2006-301211 filed in the Japan Patent Office on Nov. 7, 2006, the entire contents of which being incorporated herein by reference.

BACKGROUND OF THE INVENTION

1. Field of the Invention

This invention relates to a filter circuit and a noise reduction signal production method for a noise canceling system which are applied, for example, to a headphone for allowing a user to enjoy reproduced music or the like, a headset for reducing noise and a like apparatus and a noise canceling system which uses such a filter circuit and a noise reduction signal production method as just mentioned.

2. Description of the Related Art

An active noise reduction system (noise canceling system (noise reduction system)) incorporated in a headphone is available in the related art. Therefore, such a noise reduction system as mentioned above is hereinafter referred to as noise canceling system. Noise canceling systems which are placed in practical use at present are all implemented in the form of an analog circuit and are classified into two types including the feedback type and the feedforward type.

A noise reduction apparatus is disclosed, for example, in Japanese Patent Laid-Open No. Hei 3-214892 (hereinafter referred to as Patent Document 1). In the noise reduction apparatus of Patent Document 1, a microphone unit is provided in an acoustic tube to be attached to an ear of a user. Internal noise of the acoustic tube collected by the microphone unit is inverted in phase and emitted from an earphone set provided in the proximity of the microphone unit thereby to reduce external noise.

A noise reduction headphone is disclosed in Japanese Patent Laid-Open No. Hei 3-96199 (hereinafter referred to as Patent Document 2). In the noise reduction headphone of Patent Document 2, when it is attached to the head of a user, a second microphone is positioned between the headphone and the auditory meatus. An output of the second microphone is used to make the transmission characteristic from a first microphone, which is provided in the proximity of the ear when the headphone is attached to the head of the user and collects external sound, to the headphone same as the transmission characteristic of a path along which the external noise reaches the meatus. The noise reduction headphone thereby reduces external noise irrespective of in what manner the headphone is attached to the head of the user.

SUMMARY OF THE INVENTION

Where it is intended to form noise canceling systems of the feedback type and the feedforward type, which are composed of analog circuits in the related art, from digital circuits, if it is tried to use a sigma-delta (Σ-Δ) type analog/digital converter (hereinafter referred to simply as ADC) or a digital/analog converter (hereinafter referred to simply as DAC), then they give rise to a problem that they exhibit significant digital delay and fails in achievement of sufficient noise reduction. Although an ADC or a DAC of the sequential conversion type which can perform high speed conversion is available even in a current situation, they are actually designed for military or business applications and are expensive. Therefore, it is difficult to adopt them in a noise reduction system to be incorporated in consumer appliances.

Therefore, it is demanded to provide a noise canceling system of digitalized formation which can achieve noise reduction of a high degree of quality without using an ADC or a DAC of the sequential conversion type which can perform high speed conversion.

The present invention has been made taking notice of the fact that, by permitting leakage of an aliasing filter of an ADC/DAC to some degree making use of a passive sound insulation characteristic of a headphone housing, the delay amount by the ADC/DAC can be lowered.

According to the present embodiment, there is provided a digital filter circuit for producing a noise reduction signal for reducing noise based on a noise signal outputted from a microphone which collects the noise, including an analog/digital conversion section configured to convert the noise signal into a digital noise signal, a first digital filter section configured to perform a decimation process of the digital noise signal, an arithmetic operation processing section configured to produce a digital noise reduction signal based on the digital noise signal obtained by the decimation process, a second digital filter section configured to perform an interpolation process of the digital noise reduction signal, and a digital/analog conversion section configured to convert the digital noise reduction signal obtained by the interpolation process into an analog signal, the first digital filter section and/or the second digital filter section being configured such that a predetermined attenuation amount is obtained within a predetermined range in the proximity of a sampling frequency around the sampling frequency.

In the digital filter circuit, the predetermined or desired attenuation amount is obtained within the predetermined range in the proximity of the sampling frequency by one or both of the first digital filter section having a digital filter configuration and configured to perform a decimation process of the digital noise signal and a second digital filter section similarly having a digital filter configuration and configured to perform an interpolation process of the digital noise reduction signal.

Consequently, even where one or both of the first and second digital filter sections is formed in digitalized formation while the delay amount therein is reduced, it is possible to form a noise reduction signal for canceling noise at a suitable timing and perform reduction of the noise suitably. Accordingly, a noise canceling system can be constructed such that, since the digital filter circuit can be used therein, system design is facilitated and the performance in use is enhanced and besides noise is reduced appropriately thereby to allow reproduction with a high quality of sound.

The digital filter circuit can be applied as a filter circuit for forming a signal for reducing noise in a noise canceling system, in which the filter circuit is in the past formed as an analog circuit. Thus, the digital filter circuit can reduce processing delay without using an expensive ADC or DAC having a high processing capacity and consequently can form a signal for reducing noise at a suitable timing.

The above and other objects, features and advantages of the present invention will become apparent from the following description and the appended claims, taken in conjunction with the accompanying drawings in which like parts or elements denoted by like reference symbols.

BRIEF DESCRIPTION OF THE DRAWINGS

FIG. 5 is a view illustrating calculation expressions representative of characteristics of the noise canceling system of the feedforward type shown in FIG. 2;

FIGS. 6A, 6B and 6C are block diagrams showing an example of a configuration where an FB filter circuit of the noise canceling system of the feedback type shown in FIG. 1B is formed as a digital circuit;

FIG. 20 is a view illustrating particular examples relating to a low order FIR filter used in an FB filter circuit of the noise canceling system of FIG. 19;

FIG. 22 is a view illustrating particular examples relating to a low order FIR filter used in an FB filter circuit of the noise canceling system of FIG. 21;

DETAILED DESCRIPTION OF THE PREFERRED EMBODIMENT

Noise Canceling System

A system which actively reduces external noise, that is, a noise canceling system, begins to be popularized in headphones and earphones. Almost all noise canceling systems placed on the market are formed from analog circuits and roughly classified into the feedback type and the feedforward type in terms of the noise canceling technique.

Before a preferred embodiment of the present invention is described, examples of a configuration and operation principle of a noise canceling system of the feedback type and examples of a configuration and operation principle of a noise canceling system of the feedforward type are described with reference to FIGS. 1A to 5.

Noise Canceling System of the Feedback Type

Figure 1A:
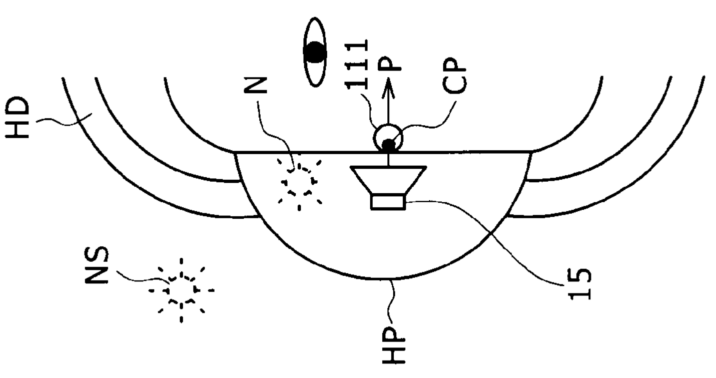
FIGS. 1A and 1B are a schematic view and a block diagram, respectively, showing a noise canceling system of the feedback type.

First, a noise canceling system of the feedback type is described. FIG. 1A shows a configuration for the right channel side where a headphone system to which a noise canceling system of the feedback type is applied is attached to the head of a user, that is, to the user head HD. Meanwhile, FIG. 1B shows a general configuration of the noise canceling system of the feedback type.

Where the feedback system is applied, generally a microphone 111 is positioned inside a headphone housing (housing section) HP as seen in FIG. 1A. An antiphase component (noise reduction signal) to a signal (noise signal) collected by the microphone 111 is fed back and used for servo control to reduce the noise which is to enter the headphone housing HP from the outside. In this instance, the position of the microphone 111 becomes a cancel point or control point CP which corresponds to the position of the ear of the user. Therefore, the microphone 111 is frequently placed at a position proximate to the ear of the user, that is, on a front face of a diaphragm of an equalizer 16 taking a noise reduction effect into consideration.

Figure 1B:
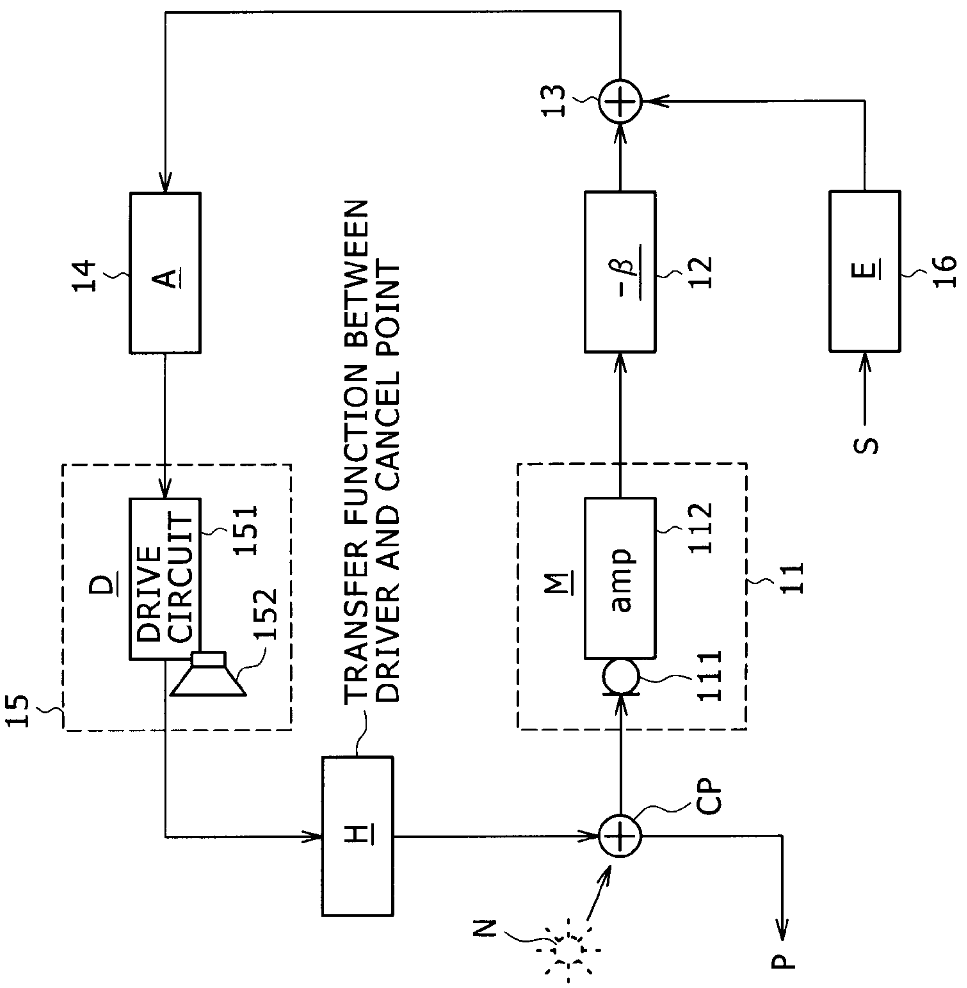

The noise canceling system of the feedback type is described more particularly with reference to FIG. 1B. The noise canceling system of the feedback type shown in FIG. 1B includes a microphone and microphone amplification section 11 including a microphone 111 and a microphone amplifier 112. The noise canceling system further includes a filter circuit (hereinafter referred to as FB filter circuit) 12 designed for feedback control, a synthesis section 13, a power amplifier 14, a driver 15 including a drive circuit 151 and a speaker 152, and an equalizer 16.

The characters A, D, M and $-\beta$ described in blocks shown in FIG. 1B represent transfer functions of the power amplifier 14, driver 15, microphone and microphone amplification section 11 and FB filter circuit 12, respectively. Similarly, the character E in the block of the equalizer 16 represents the transfer function of the equalizer 16 to be multiplied to a signal S of an object of hearing, and the character H of a block placed between the driver 15 and the cancel point CP represents the transfer function of the space from the driver 15 to the microphone 111, that is, the transfer function between the driver and the cancel point. The transfer functions mentioned are represented in complex representations.

Referring to FIGS. 1A and 1B, the character N represents noise entering from a noise source NS on the outside to a portion around the position of the microphone in the headphone housing HP, and the character P represents the sound pressure or output sound coming to the ear of the user. The cause of the entrance of the noise N into the headphone housing HP is, for example, sound leaking as a sound pressure from a gap of the ear pad of the headphone housing HP or sound transmitted to the inside of the housing as a result of vibration of the headphone housing HP caused by such sound pressure applied thereto.

Figures 3, 4:
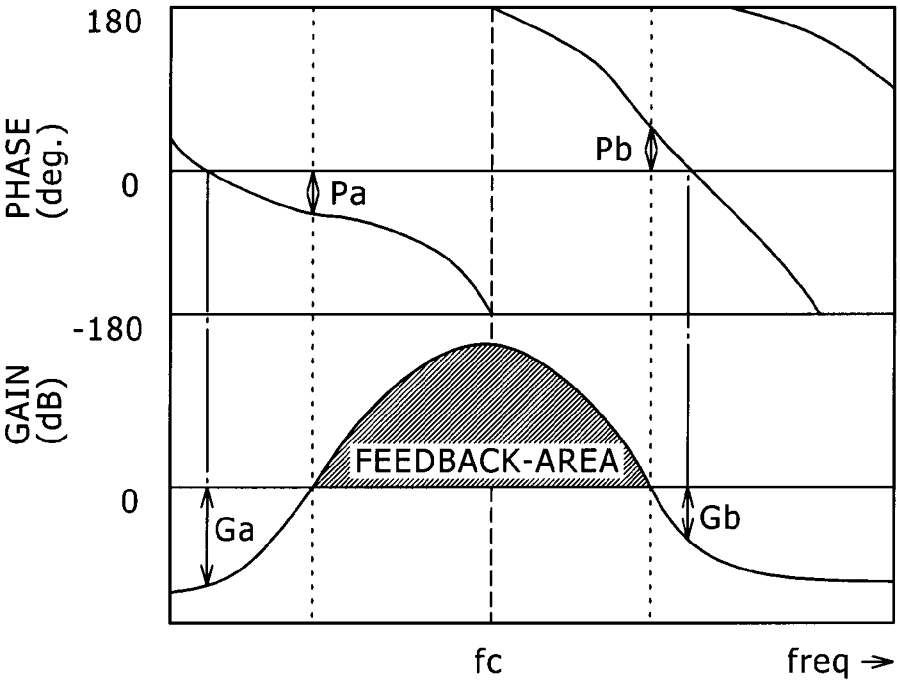
FIG. 3 is a view illustrating calculation expressions representative of characteristics of the noise canceling system of the feedback type shown in FIG. 1.
FIG. 4 is a board diagram illustrating a phase margin and a gain margin in the noise canceling system of the feedback type.

At this time, the sound pressure P coming to the ear of the user in FIG. 1B can be represented by an expression (1) in FIG. 3. If attention is paid to the noise N in the expression (1) in FIG. 3, it can be recognized that the noise N attenuates to $1/(1+ADHM\beta)$. In order for the system of the expression (1) of FIG. 3 to operate stably as a noise canceling mechanism within a noise reduction object frequency band, it is necessary for an expression (2) in FIG. 3 to be satisfied.

Generally, since the absolute value of the product of the transfer functions in a noise canceling system of the feedback type is higher than 1 ($1 \ll ADHM\beta$), the stability of the system according to the expression (2) of FIG. 3 can be interpreted in the following manner together with decision of the stability of Nyquist in old control theories.

An "open loop" produced when a loop relating to the noise N is cut at one place ($-ADHM\beta$) in FIG. 1B is considered. For example, if the cut portion is provided between the microphone and microphone amplification section 11 and the FB filter circuit 12, then an "open loop" can be formed. This open loop has such a characteristic as is represented, for example, by such a board diagram as seen in FIG. 4.

Where this open loop is selected as an object, from the stability decision of Nyquist, two conditions of (1) that, when the phase passes a point of 0 degree, the gain must be lower than 0 dB (0 decibel) and (2) that, when the gain is higher than 0 dB, the phase must not include a point of 0 degree.

If any of the conditions (1) and (2) above is not satisfied, then positive feedback is applied to the loop, resulting in oscillation (howling) of the loop. In FIG. 4, reference characters Pa and Pb individually represent a phase margin, and Ga and Gb individually represent a gain margin. Where such margins are small, the possibility of oscillation is high depending upon the personal differences among users who utilize a headphone to which the noise canceling system is applied and upon the dispersion in mounting of the headphone.

In particular, the axis of abscissa in FIG. 4 indicates the frequency while the axis of ordinate indicates the gain and the phase at lower and upper halves thereof, respectively. Then, when the phase passes a point of 0 degree, as seen from the gain margins Ga and Gb in FIG. 4, if the gain is lower than 0 dB, then positive feedback is applied to the loop, resulting in oscillation. However, when the gain is equal to or higher than 0 dB, unless the phase does not include a point of 0 degree, positive feedback is applied to the loop, resulting in oscillation, as seen from the phase margins Pa and Pb in FIG. 4.

Now, reproduction of necessary sound from the headphone in which the noise securing system of the feedback type shown in FIG. 1B is incorporated is described in addition to the noise reduction function described above. The input sound S in FIG. 1B is a general term of a sound signal to be reproduced originally by the driver of the headphone such as, for example, a music signal from a music reproduction apparatus, sound of the microphone outside the housing (where the headphone is used as a hearing aid function) or a sound signal by communication such as telephone communication (where the headphone is used as a headset).

If attention is paid to the input sound S in the expression (1) in FIG. 3, the transfer function E of the equalizer 16 can be represented by the expression (3) in FIG. 3. Further, if also the transfer function E of the equalizer 16 in the expression (3) of FIG. 3 is taken into consideration, the sound pressure P of the noise canceling system of FIG. 1B can be represented by an expression (4) in FIG. 3.

If it is assumed that the position of the microphone 111 is very proximate to the position of the ear, then since the character H represents the transfer function from the driver 15 to the microphone (ear) 111 and the characters A and D represent the transfer functions of the power amplifier 14 and the driver 15, respectively, it can be recognized that a characteristic similar to that of an ordinary headphone which does not have the noise reduction function is obtained. It is to be noted that the transfer function E of the equalizer 16 in this instance is substantially equivalent to an open loop characteristic as viewed on the frequency axis.

Noise Canceling System of the Feedforward Type

Figures 2A, 2B:
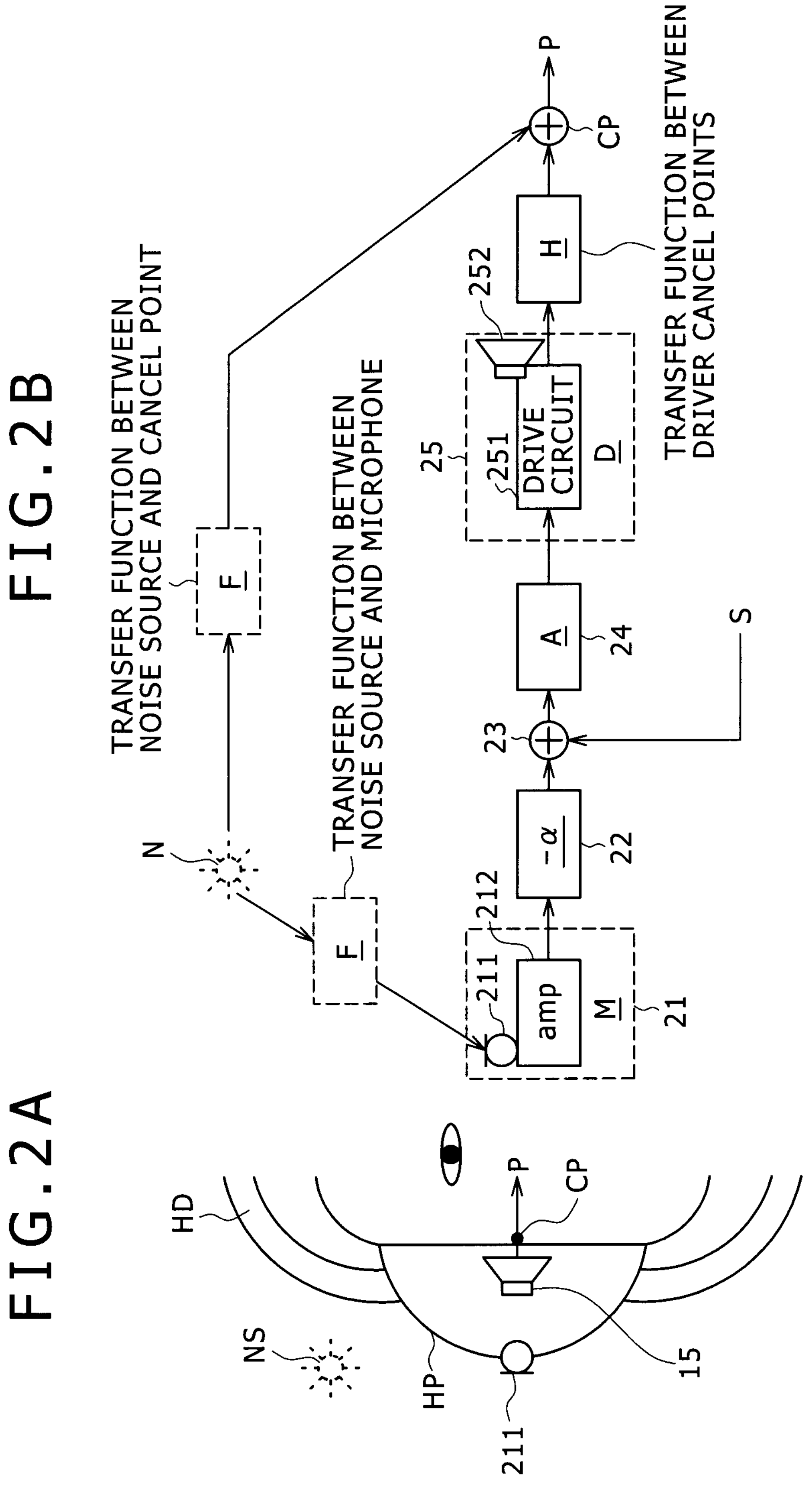
FIGS. 2A and 2B are a schematic view and a block diagram, respectively, showing a noise canceling system of the feedforward type.

Now, a noise canceling system of the feedforward type is described. FIG. 2A shows a configuration for the right channel side where a headphone system to which a noise canceling system of the feed forward type is applied is attached to the head of a user, that is, to a user head HD. Meanwhile, FIG. 2B shows a general configuration of the noise canceling system of the feedforward type.

In the noise canceling system of the feedforward type, a microphone 211 is basically disposed outside a headphone HP as seen in FIG. 2A. Then, noise collected by the microphone 211 is subjected to a suitable filtering process and then reproduced by a driver 25 provided inside the headphone housing HP so that the noise is canceled at a place proximate to the ear.

The noise canceling system of the feedforward type is described more particularly with reference to FIG. 2B. The noise canceling system of the feedforward type shown in FIG. 2B includes a microphone and microphone amplification section 21 including a microphone 211 and a microphone amplifier 212. The noise canceling system further includes a filter circuit (hereinafter referred to as FF filter circuit) 22 designed for feedforward control, a synthesis section 23, a power amplifier 24, and a driver 25 including a drive circuit 251 and a speaker 252.

Also in the noise canceling system of the feedforward type shown in FIG. 2B, the characters A, D and M described in blocks represent transfer functions of the power amplifier 24, driver 25 and microphone and microphone amplification section 21, respectively. Further, in FIG. 2, the character N represents an external noise source. The principal reason in entrance of noise into the headphone housing HP from the noise source N is such as described hereinabove in connection with the noise canceling system of the feedback type.

Further, in FIG. 2B, the transfer function from the position of the external noise N to the cancel point CP, that is, the transfer function between the noise source and the cancel point, is represented by the character F. Further, the transfer function from the noise source N to the microphone 211, that is, the transfer function between the noise source and the microphone, is represented by the character F'. Furthermore, the transfer function from the driver 25 to the cancel point (ear position) CP, that is, the transfer function between the driver and the cancel point, is represented by the character H.

Then, if the transfer function of the FF filter circuit 22 which makes the core of the noise canceling system of the feedforward type is represented by $-\alpha$, then the sound pressure or output sound P coming to the ear of the user in FIG. 2B can be represented by an expression (1) in FIG. 5.

Here, if ideal conditions are considered, then the transfer function F between the noise source and the cancel point can be presented by an expression (2) in FIG. 5. Then, if the expression (2) in FIG. 5 is substituted into the expression (1) in FIG. 5, then since the first term and the second term cancel each other, the sound pressure P in the noise canceling system of the feedforward type shown in FIG. 2B can be represented by an expression (3) in FIG. 5. From the expression (3), it can be recognized that the noise is canceled while only the music signal or the object sound signal or the like to be heard remains and sound similar to that in ordinary headphone operation can be enjoyed.

Actually, however, it is difficult to obtain a configuration of a complete filter having such transfer functions that the expression (2) illustrated in FIG. 5 is satisfied fully. Particularly in middle and high frequency regions, usually such an active noise reduction process as described above is not performed but passive sound interception by the headphone housing is applied frequently from such reasons that the individual differences are great in that the shape of the ear differs among different persons and the attaching state of a headphone differs among different persons and that the characteristics vary depending upon the position of noise and the position of the microphone. It is to be noted that the expression (2) in FIG. 5 signifies, as apparent from the expression itself, that the transfer function from the noise source to the ear position can be imitated by an electric circuit including the transfer function α.

It is to be noted that, different from that in the noise canceling system of the feedback type, the cancel point CP in the noise canceling system of the feedforward type shown in FIGS. 2A and 2B can be set to an arbitrary ear position of the user as seen in FIG. 2A. However, in an ordinary case, the transfer function a is fixed and is determined aiming at some target characteristic in advance at a design stage. Therefore, there is the possibility that such a phenomenon may occur that, since the shape of the ear differs among different users, a sufficient noise cancel effect is not achieve or a noise component is added but not in an inverted phase, resulting in generation of abnormal sound.

From those, the noise canceling systems of the feedback type and the feedforward type generally have different characteristics in that, while the noise canceling system of the feedforward type is low in possibility of oscillation and hence is high in stability, it is difficult to obtain a sufficient attenuation amount whereas the noise canceling system of the feedforward type may require attention to stability of the system while a great attenuation amount can be expected.

A noise reduction headphone which uses an adaptive signal processing technique is proposed separately. In the case of a noise reduction headphone which uses the adaptive signal processing technique, a microphone is provided on both inside and outside a headphone housing. The inside microphone is used to analyze an error signal for cancellation with a filter processing component and produce and update a new adaptive filter. However, since noise outside of the headphone housing is basically processed by a digital filter and reproduced, the noise reduction headphone generally has a form of a feedforward system.

Necessity for and Problems of Digitalized Formation of a Noise Canceling System

While noise canceling systems formed from analog circuits of the feedback type and the feedforward type are implemented as described above, it is demanded to form such noise canceling systems from digital circuits. In the following, the necessity for and problems of digitalized formation of a noise canceling system are described particularly. Further, the invention which solves the problems is described particularly.

It is to be noted that, in the following description, for simplified description, principally an application to a noise canceling system of the feedback type which exhibits a high noise attenuation effect is described as an example. However, also with regard to a noise canceling system of the feedforward type, the necessity for and problems in digitalization exist, and the present invention can solve the problems similarly.

Necessity for Digitalized Formation of a Noise Canceling System

First, the necessity for digitalized formation of a noise canceling system is described. If the FB filter circuit 12 which is a transfer function (−β) section in the noise canceling system of the feedback type can be formed in digitalized formation, then such merits as described in (1) to (4) below can be enjoyed.

In particular, (1) a system which allows automatic selection or manual operation by a user of a plurality of modes and the use performance as viewed from the user is raised. (2) As a digital filter which allows fine control is used, control quality of a high degree of accuracy which exhibits a reduced dispersion can be achieved, resulting in increase of the noise reduction amount and the reduction frequency band.

Further, (3) since the filter shape can be changed by modification to software for an arithmetic operation processing device (digital signal processor (DSP)/central processing unit (CPU)) without changing the number of parts, alteration involved in change of the system design or device characteristics is facilitated. (4) Since the same ADC/DAC and DSP/CPU are used also for an external input such as music reproduction or telephone conversation, high sound quality reproduction can be anticipated by applying digital equalization of a high degree of accuracy also for such external input signals.

If the FB filter circuit 12 can be formed in digitalized formation in this manner, then flexible control becomes possible for various cases, and a system can be configured which can cancel noise in high quality irrespective of a user who uses the system.

Problems in Digitalized Formation of a Noise Canceling System

However, as described hereinabove, only a system whose portion corresponding to the FB filter circuit 12 is formed from an analog circuit is placed in practical use as a noise canceling system of the feedback type. It is possible to configure the FB filter circuit 12, which is formed from an analog circuit, otherwise from a digital circuit by using an ADC, a DSP or a CPU which forms a digital filter processing mechanism (arithmetic operation processing section), a DAC and so forth.

However, the FB filter circuit 12 having a configuration of a digital circuit needs much time for processing. Therefore, the FB filter circuit 12 gives rise to delay of a signal of a processing object and fails to appropriately cancel noise. This makes a factor of obstruction to the digitalized formation. If the factor of obstruction to the digitalized formation is studied more particularly, then it is considered that the delay of a signal described above is caused principally by the delay by the ADC and the DAC inserted forwardly and backwardly of the arithmetic operation processing section (arithmetic operation processing apparatus) formed from a DSP and a CPU (hereinafter referred to as DSP/CPU) rather than by the digital filter processing mechanism (arithmetic operation processing section for producing a noise reduction signal for reducing noise) formed from a DSP/CPU.

FIGS. 6A, 6B and 6C show an example of a configuration of the FB filter circuit 12 of the noise canceling system of the feedback type described hereinabove with reference to FIG. 1B where the FB filter circuit 12 is formed in digitalized formation. While the FB filter circuit 12 is shown in a single block also in FIG. 1B, in order to form the FB filter circuit 12 which is shown in a single block in FIG. 6A in digitalized formation, the FB filter circuit 12 is formed from an ADC 121, a DSP/CPU 122 and a DAC 123 as seen in FIG. 6B. Although a digital filter can be configured comparatively freely as software in the DSP/CPU 122, it is influenced much by delay by filters built in the ADC 121 and the DAC 123.

Here, the ADC 121 is a block for converting a signal (noise signal) collected by the microphone 111 and amplified by the microphone amplifier 112 into a digital signal, that is, a digital noise signal. Meanwhile, the DSP/CPU 122 is a block which forms a noise reduction signal having a phase opposite to that of the noise signal and capable of canceling the noise signal taking the transfer functions of the associated circuit sections and the transfer functions between the driver and the cancel point and so forth into consideration. Further, the DAC 123 is a block which converts a noise reduction signal in the form of a digital signal formed by the DSP/CPU 122 into an analog signal.

If the configuration of the FB filter circuit 12 shown in FIG. 6B is represented functionally, then it can be represented as being formed from a digital filter section 121, 123 for generating delay L and a digital filter section 122 formed from the DSP/CPU. Then, in the digitalized FB filter circuit 12, a delay of L samples is produced compulsorily for a sampling frequency Fs as seen in FIG. 6C. Consequently, even if a digital filter is designed freely by the DSP/CPU, this component is inserted in series without fail as represented by an equivalent block in FIG. 6C. It is to be noted that, in applicable figures, the [sample] unit is described briefly as [smp].

For example, as a general example, if it is assumed that the delay amount generated in the inside of each of devices of the ADC and the DAC whose sampling frequency Fs is Fs=48 kHz is 20 samples for the sampling frequency Fs, then delay of totaling 40 samples is generated by the ADC and the DAC in the FB filter circuit 12 even if arithmetic operation relating to the DSP/CPU and so forth is not performed. As a result, the delay of 40 samples is applied as a delay of the open loop to the entire system.

Figure 7A:
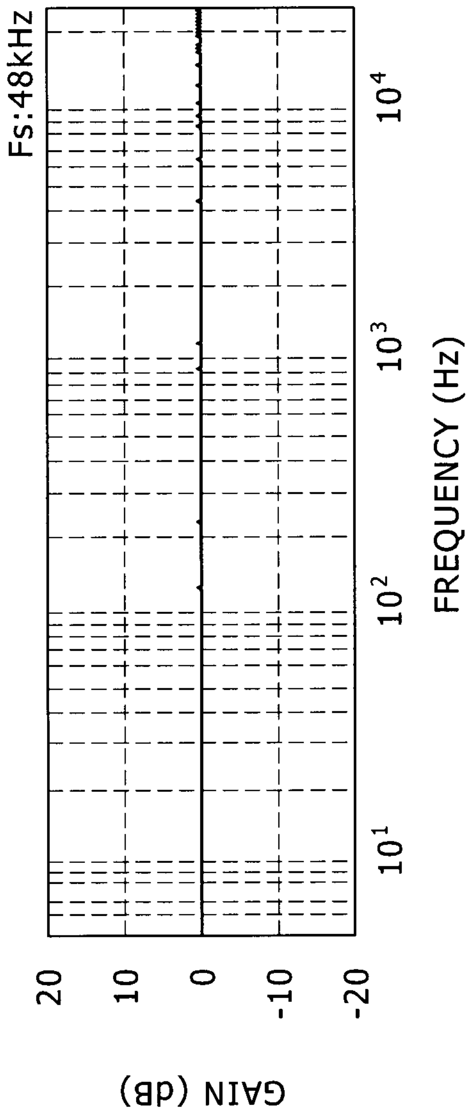
FIGS. 7A and 7B are diagrams illustrating a gain and a phase corresponding to a delay amount of 40 samples where the sampling frequency is 48 kHz.
Figure 7B:
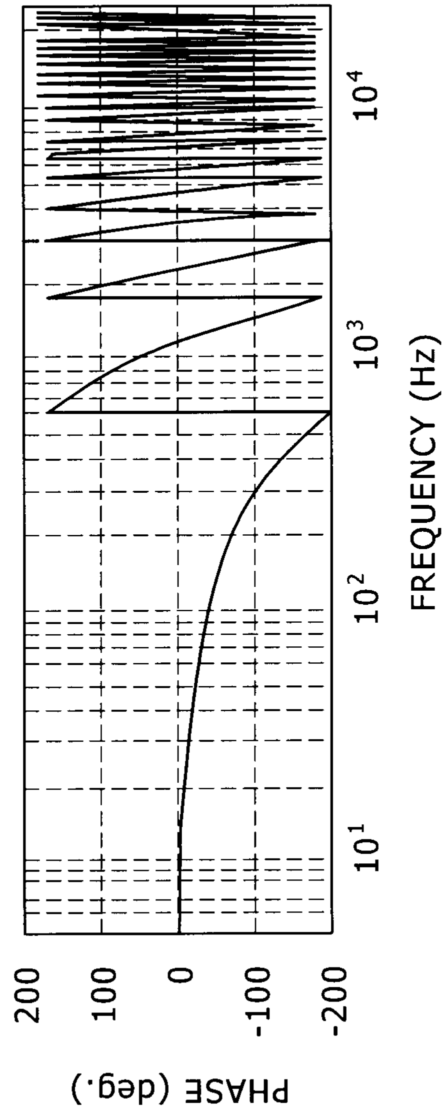
Figures 8A, 8B, 8C:
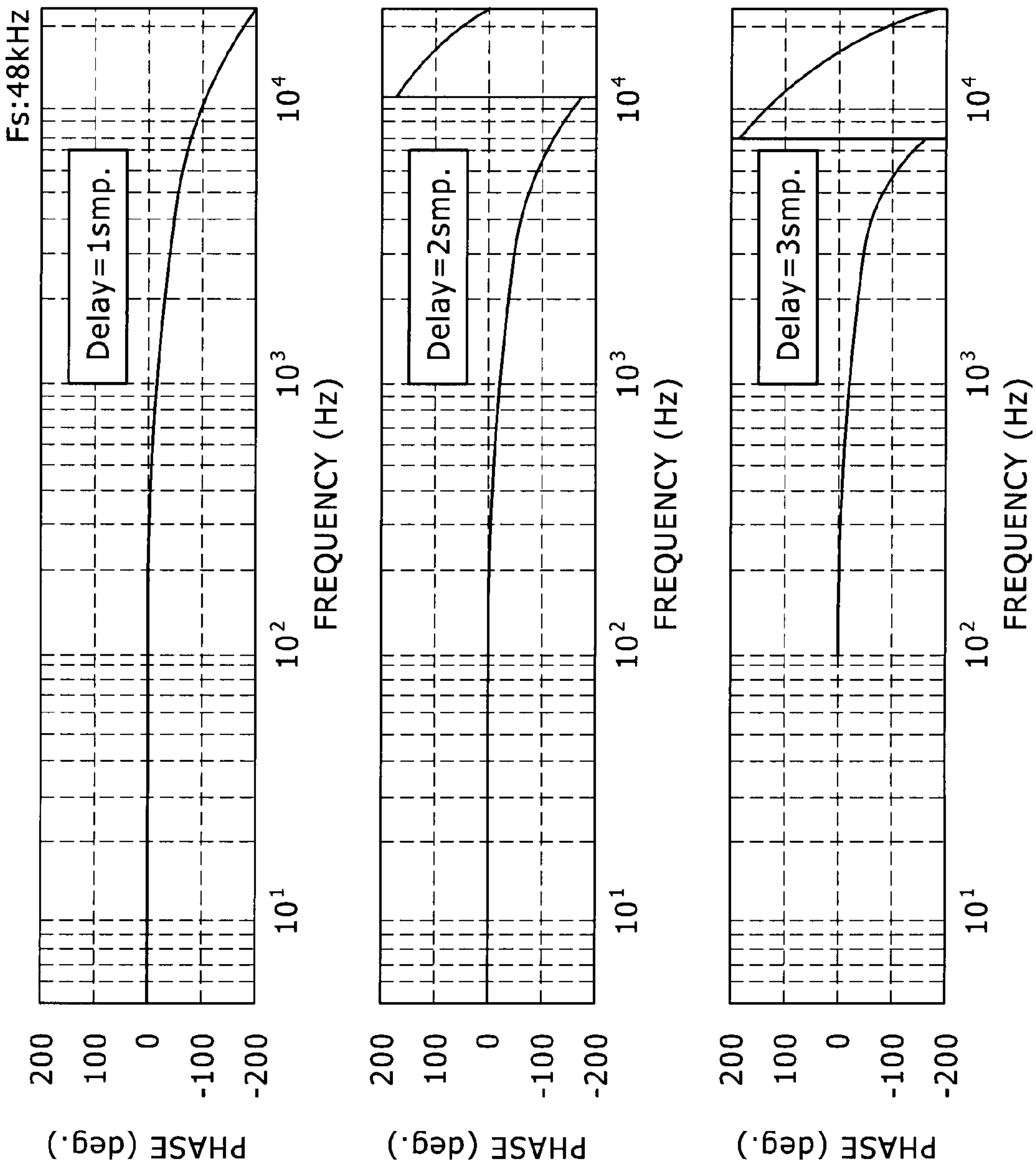
FIGS. 8A, 8B and 8C are diagrams illustrating the state of the phase where the sampling frequency is 48 kHz and the delay amount is one sample, two samples and three samples, respectively.
Figure 9A:
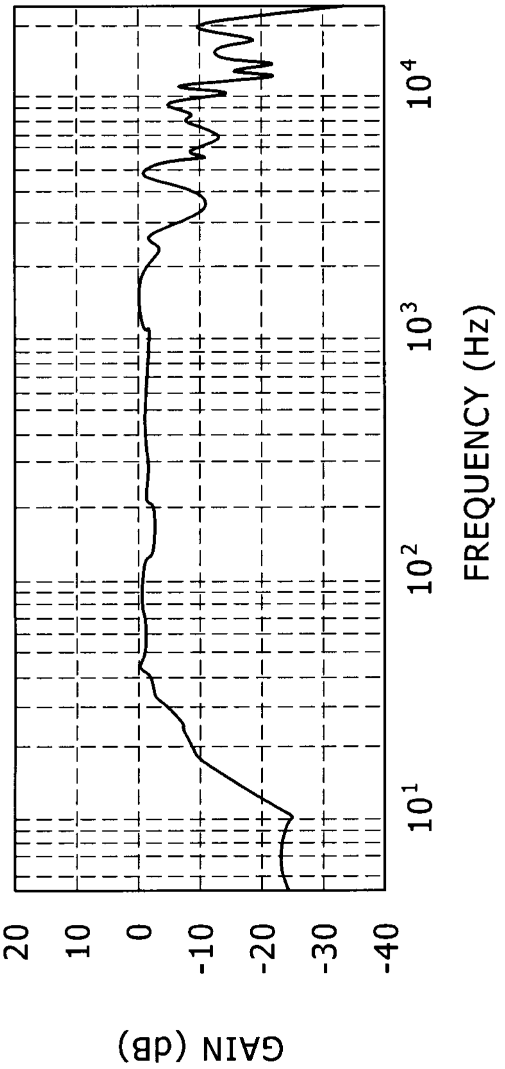
FIGS. 9A and 9B are diagrams illustrating measurement values of the transfer function from a driver to a microphone in the noise canceling system of the feedback type.

The delay amount involved in the FB filter circuit 12 is described more particularly using actual measurement values. FIGS. 7A and 7B illustrate a gain and a phase corresponding to the delay amount of 40 samples where the sampling frequency Fs is Fs=48 kHz. Meanwhile, FIGS. 8A to 8C illustrate the state of the phase where the delay amount is 1 sample, 2 samples and 3 samples, respectively, while the sampling frequency Fs is Fs=48 kHz. Further, FIGS. 9A and 9B illustrate measurement values of the transfer function from the driver to the microphone in the noise canceling system of the feedback type.

More particularly, in FIG. 7A, the axis of abscissa indicates the frequency, and the axis of ordinate indicates the gain. Meanwhile, in FIG. 7B, the axis of abscissa indicates the frequency, and the axis of ordinate indicates the phase. As seen from FIG. 7B, rotation of the phase starts from several tens Hz, and the phase rotates by a great amount until the frequency comes to Fs/2 (24 kHz), that is, to one half the sampling frequency Fs.

This can be recognized readily if it can be understand that the delay by one sample at the sampling frequency Fs=48 kHz corresponds to a phase delay by 180 degrees (π) at the Fs/2 frequency as seen in FIG. 8A and similarly the delays by two samples and three samples correspond to 360 degrees (2π) and 540 degrees (3π) as seen from FIGS. 8B and 8C, respectively. In other words, in the example, as the delay amount increases by one sample, the phase delay increases by π.

Figure 9B:
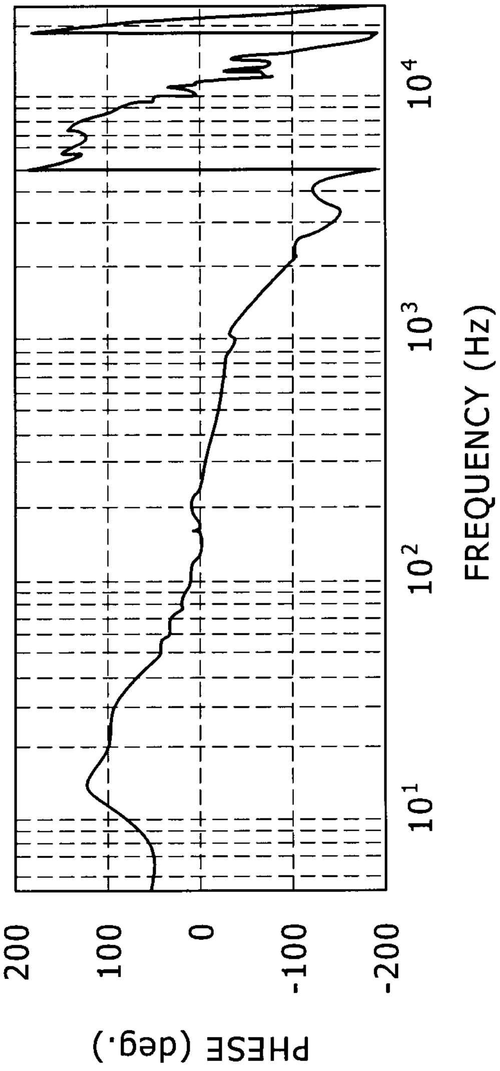

Meanwhile, in the noise canceling system of the feedback type, as seen also in FIG. 1A, since the position of the microphone 111 is set to a place in the proximity of the front face of the driver 15, the distance between them is small, and it can be recognized that the transfer function from the driver to the microphone exhibits a comparatively small amount of phase rotation as seen in FIG. 9B. This is apparent also from comparison between FIG. 7B and FIG. 9B.

The transfer function from the driver to the microphone in the noise canceling system of the feedback type whose characteristics are illustrated in FIGS. 9A and 9B corresponds to ADHM in the expressions (1) and (2) in FIG. 3, and a result of multiplication between this transfer function and the −β characteristic of the FB filter circuit 12 on the frequency axis as it is makes an open loop. The characteristic of this open loop must satisfy the two conditions including the condition (1) that, when the phase passes a point of 0 degree, the gain must be lower than 0 dB (0 decibel) and the condition (2) that, when the gain is higher than 0 dB, the phase must not include a point of 0 degree.

If the phase characteristic of FIG. 7B is examined again here, then it can be seen that the phase rotates one rotation (2π) in the proximity of 1 kHz after it stars from 0 degree. In addition, also in the ADHM characteristic of FIG. 9B (in the transfer characteristic from the driver to the microphone), phase delay exists depending upon the distance from the driver to the microphone.

If the block diagram or structure diagram shown in FIG. 6C which represents the FB filter circuit 12 functionally is examined, then while the filter section 122 (implemented using a DSP/CPU) which can be designed freely is connected in series to the delay component by the DSP/CPU, it is basically difficult to design a filter having a leading phase in the digital filter section 122 from the law of casualty. However, depending upon the configuration of the filter shape, it may be possible to compensate for a "partial" phase lead only within a particular frequency band. However, it is impossible to form such a phase leading circuit over a wide frequency band which compensates for phase rotation by the delay component by the ADC/DAC.

From this, it can be recognized that, even if a preferable digital filter is designed by the DSP/CPU 122 in the FB filter circuit 12 (−β block), the frequency band within which a noise reduction effect can be obtained from the feedback configuration in this instance is limited to less than approximately 1 kHz at which the phase rotates by one rotation, and if an open loop which incorporates also the ADHM characteristic is assumed and a phase margin and a gain margin are taken into account, then the attenuation amount and the attenuation frequency band are further narrowed.

Solutions to the Problems Involved in Digitalized Formation of a Noise Canceling System From the study of the problems described above, it can be recognized that, if the delay time generated in the ADC 121 and the DAC 123 used in the FB filter circuit 12 used in the noise canceling system of the feedback type is decreased, then the phase rotation generated in the FB filter circuit 12 can be reduced, which facilitates designing of the FB filter circuit 12 and makes it possible to increase the noise reduction effect frequency bandwidth.

However, if an ADC or a DAC of the sequential conversion type which can perform high speed conversion is used, then a high cost may be required, and the use of such an ADC or a DAC is not practical. Therefore, the present invention makes it possible to reduce the delay time even where a comparatively less expensive sigma-delta type ADC or DAC which is generally used frequently is used.

Principal Factors of Generation of Delay

First, principal factors which cause delay in the ADC 121 and the DAC 123 in the FB filter circuit 12 are made clear.

Figures 10A, 10B:
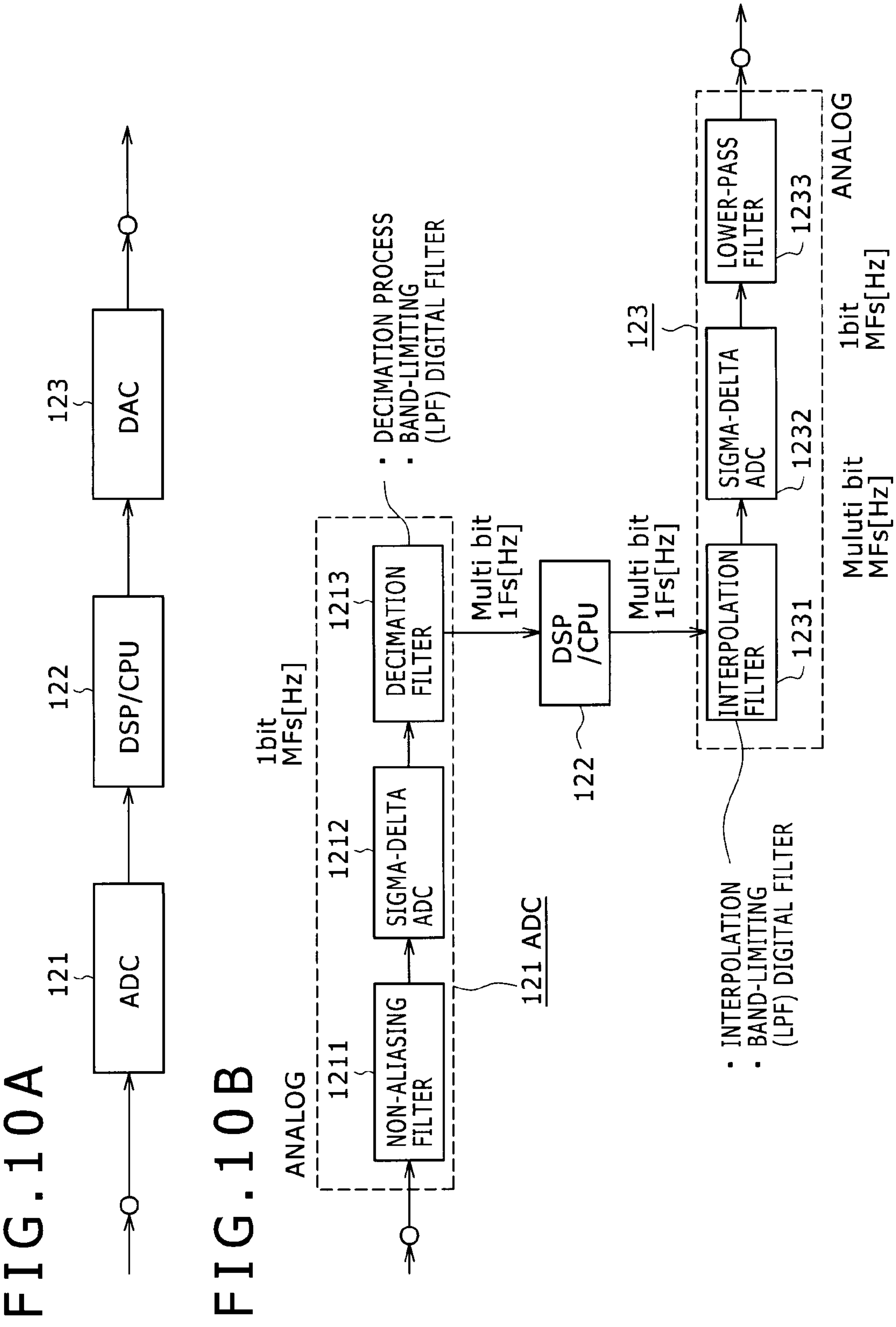
FIGS. 10A and 10B are block diagrams showing a configuration of the FB filter circuit, particularly of an ADC and a DAC.

As seen in FIGS. 6B and 10A, the FB filter circuit 12 includes an ADC 121, a DSP/CPU section 122, and a DAC123. As seen in FIG. 10B, the ADC 121 includes a non-aliasing filter 1211, a sigma-delta (Σ-Δ) ADC section 1212, and a decimation filter 1213. Meanwhile, the DAC 123 includes an interpolation filter 1231, a sigma-delta (Σ-Δ) DAC section 1232, and a low-pass filter 1233.

Generally, both of the ADC 121 and the DAC 123 use an oversampling method and sigma-delta modulation in which a 1-bit signal is used. For example, where an analog input is subjected to a digital signal process by the DSP/CPU section 122, it is converted into 1 Fs/multi-bits (in most cases, 6 bits to 24 bits). However, according to the Σ-Δ method, the sampling frequency Fs [Hz] is in most cases raised to MFs [Hz] of M times to perform oversampling.

In the FB filter circuit 12 shown in FIG. 10B, the non-aliasing filter 1211 provided at the entrance of the ADC 121 and the low-pass filter 1233 provided at the exit of the DAC 123 prevent a signal in a frequency band exceeding ½ (one half) each sampling frequency Fs from being inputted and outputted, respectively. Actually, however, since both of the non-aliasing filter 1211 and the low-pass filter 1233 are formed from analog devices, it is difficult to obtain a steep attenuation characteristic in the proximity of Fs/2 (one half the sampling frequency Fs).

In particular, in FIG. 10B, the decimation filter 1213 is included in the ADC side while the interpolation filter 1231 is included in the DAC side, and the decimation filter 1213 and the interpolation filter 1231 are used to perform a decimation process and an interpolation process, respectively. Simultaneously, in the decimation filter 1213 and the interpolation filter 1231, a high-order steep digital filter is used to apply band limitation (LPF) to decrease the burden on the non-aliasing filter 1211 which accepts an analog signal and the low-pass filter 1233 which outputs an analog signal, respectively.

Delay occurring in the ADC 121 and the DAC 123 is generated almost by a high-order digital filter in the decimation filter 1213 and the interpolation filter 1231. In particular, since a filter having a high order number (in the case of an FIR filter, having a great number of taps) in a region having the sampling frequency of MFs [Hz] is used in order to obtain a characteristic which is steep in the proximity of Fs/2, delay is generated. In this digital filter section, in order to avoid a bad influence of deterioration of the time waveform by phase distortion, an FIR filter having a linear phase characteristic is used. Especially, there is a tendency to favorably use an FIR filter based on a moving average filter which can implement an interpolation characteristic by a SINC function (sin(x)/x).

Figure 11:
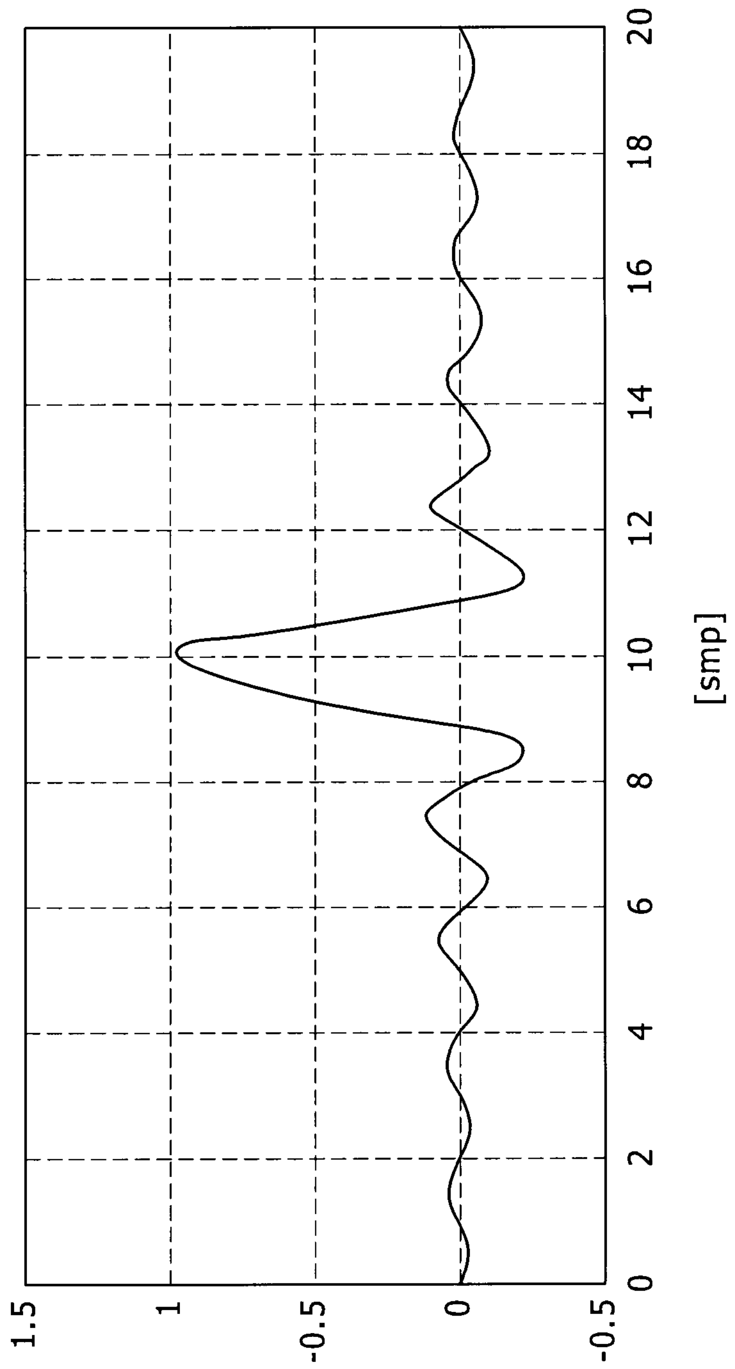
FIG. 11 is a diagram illustrating a coefficient characteristic of a linear phase type FIR filter.

It is to be noted that, in the case of a filter of the linear phase type, the time of one half the filter length almost makes a delay amount. For example, in an FIR filter of the linear phase type having such coefficients as illustrated in FIG. 11, that is, such coefficients that the filter length is 20 samples and the coefficient is 1 at 10 sample while the coefficient is zero or a value proximate to zero in the other portion, the substantial delay amount is 10 samples. An FIR filter can naturally represent a characteristic which exhibits a steeper inclination and provides a higher attenuation effect as the order number (tap number) increases.

Since a filter of a low order number does not provide a sufficient attenuation amount but provide much leak and is influenced much by aliasing, usually it is not used very much. However, where a filter of a low order number is used in the noise canceling system of the feedback type, it becomes possible to use an FIR filter which satisfies such conditions as hereinafter described, and as a result, the delay time can be reduced.

As the delay time decreases, the phase rotation decreases as described hereinabove with reference to FIG. 7. As a result, when the FB filter circuit 12 is designed so as to make such a composite open loop characteristic as described hereinabove with reference to FIG. 4, the bandwidth within which the characteristic is higher than 0 dB can be expanded. Consequently, a high effect can be achieved in the frequency band and the attenuation characteristic of the noise canceling mechanism. In addition, it can be estimated readily that also the degree of freedom increases upon production of a filter.

Applicability of a Filter of a Low Order Number

Here, examples of a digital low-pass filter (LPF) in the decimation filter 1213 of the actual ADC 121 and the interpolation filter 1231 of the actual DAC 123 are described.

It is to be noted that, in FIGS. 12B, 13B, 14B and 15B, the characteristic along the frequency axis is represented by a log scale while, in FIGS. 12C, 13C, 14C and 15C, the characteristic along the frequency axis is represented by a linear scale.

Now, the sampling frequency Fs is set to Fs=96 [kHz] and the multiple M of the oversampling is set to 256. In this instance, FIGS. 12B and 12C illustrate frequency amplitude characteristics of the SINC filter up to 2 Fs (192 kHz), for example, when a moving average filter of a filter length of 512 samples (in an FIR structure, all coefficients have a value of 1/512) is applied on 256 Fs [Hz] (=256×96 kHz) as seen in FIG. 12A.

In this instance, as regards FIR arithmetic operation in a sampling frequency region of 256 Fs, since the delay time is one half the filter length as described hereinabove, the delay time in this instance corresponds to 256 samples which are one half the FIR filter length of 512 samples. Since the delay time of FIR arithmetic operation in the sampling frequency region of 256 Fs corresponds to 256 samples, if the delay time is converted into delay time in the Fs (96 kHz) region, the delay corresponding to one sample occurs.

This is common to the ADC and the DAC. In this instance, however, as can be recognized from FIGS. 12*b* and 12*c*, the amplitude attenuates only approximately −20 dB also in a frequency band higher than Fs/2 (48 kHz). Therefore, the digital LPF shown in FIG. 12 is low in practicality. Therefore, it is a possible idea to increase, regarding the FIR filter as one stage, the number of stages successively to increase the attenuation characteristic.

Figure 12A:
FIGS. 12A, 12B and 12C are a block diagram and diagrams illustrating a frequency amplitude characteristic where a FIR moving average filter is single.
Figure 12B:
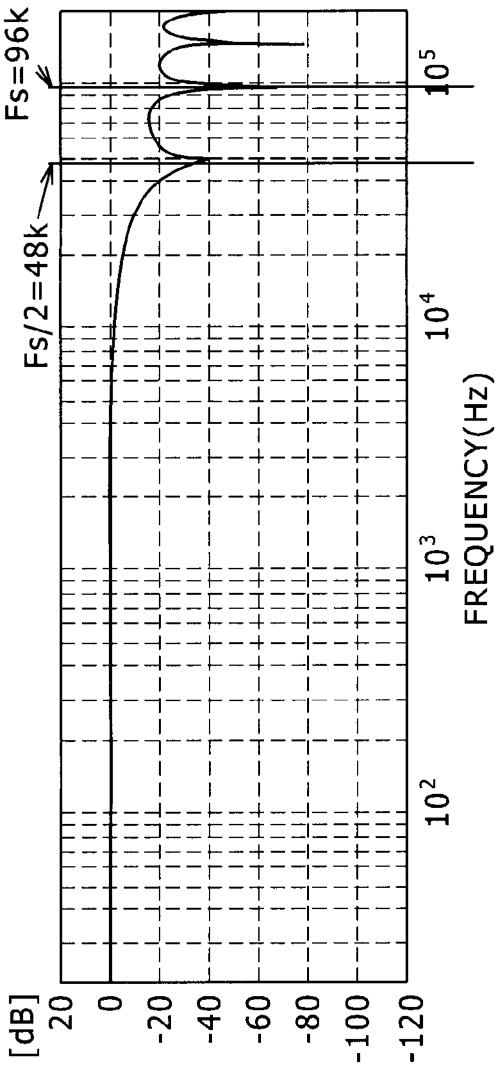
Figure 12C:
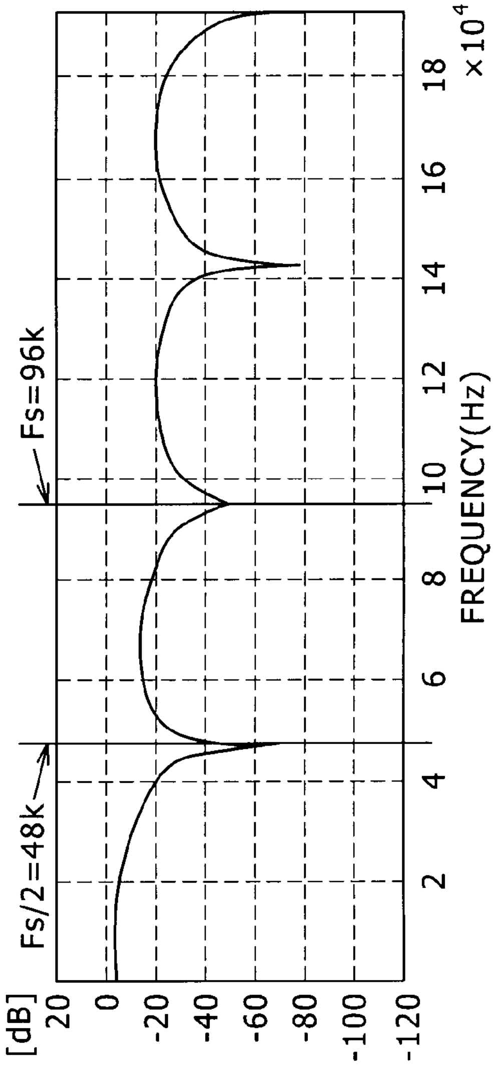
Figure 13A:
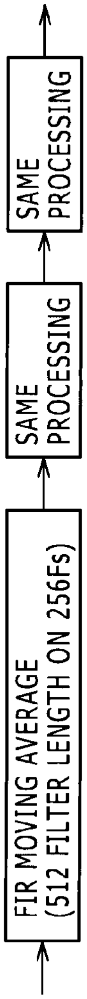
FIGS. 13A, 13B and 13C are a block diagram and diagrams illustrating a frequency amplitude characteristic where FIR moving average filters are three.
Figure 13B:
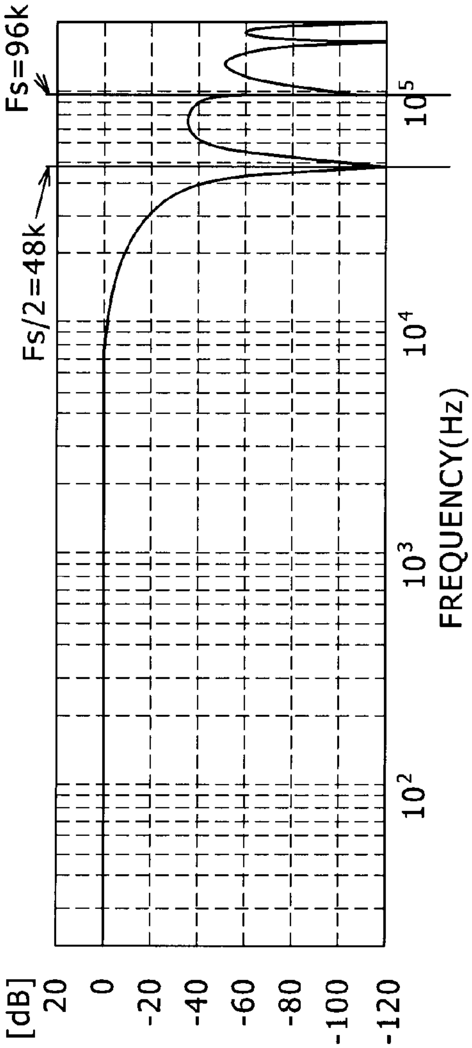
Figure 13C:
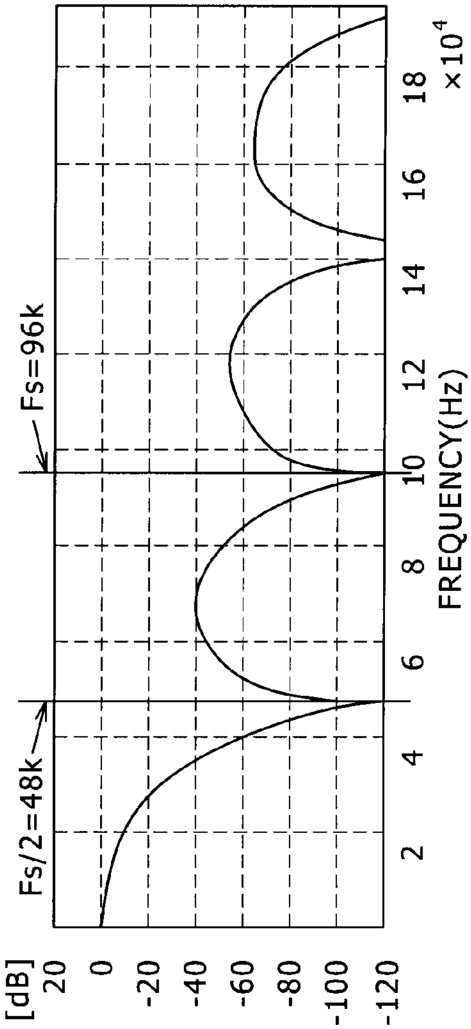

For example, it is considered here to connect the FIR moving average filter shown in FIG. 12A at three stages in series as seen in FIG. 13A. Where the FIR moving average filters are connected in this manner, higher attenuation characteristics can be obtained in the frequency band higher than Fs/2 (48 kHz) as seen in FIGS. 13*b* and 13*c*. Consequently, the influence of aliasing on the ADC and the DAC can be reduced.

In this instance, since the delay amount is one sample by Fs (96 kHz) sampling per one stage, the total delay corresponds to 3 samples. Where the ADC and the DAC are used for music signal reproduction or the like of an ordinary compact disk (CD), greater amounts of filter attenuation than those in the case of FIGS. 13B and 13C may be required. Therefore, the number of stages is further increased, or the order number of the FIR filter is increased. As a result, the delay time tends to increase.

However, a player for a CD or the like is used only for reproduction and it does not matter even if some delay amount exists, different from other apparatus which may require real time control. Further, the digital filter for aliasing prevention need not necessarily be a SINC filter of the moving average type having an equal coefficient value as a coefficient of the FIR. Also it is possible to obtain a desired characteristic by using weighting while the linear phase characteristic is maintained.

Figure 14A:
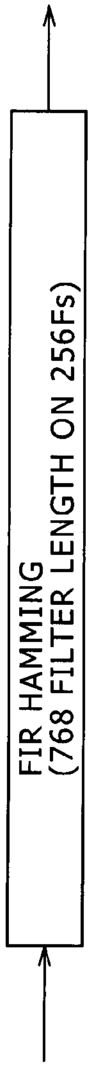
FIGS. 14A, 14B and 14C are a block diagram and diagrams illustrating a frequency amplitude characteristic where a FIR Hamming filter is single.
Figure 14B:
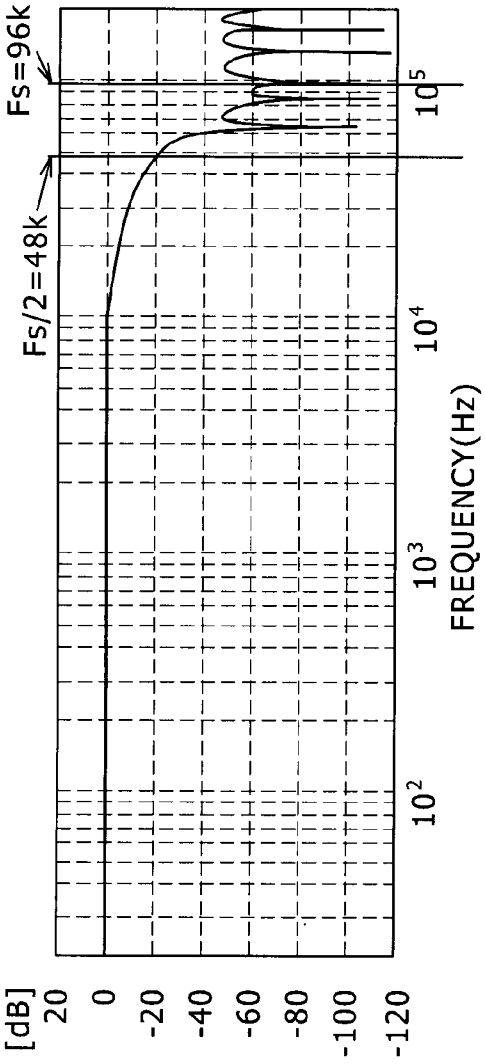
Figure 14C:
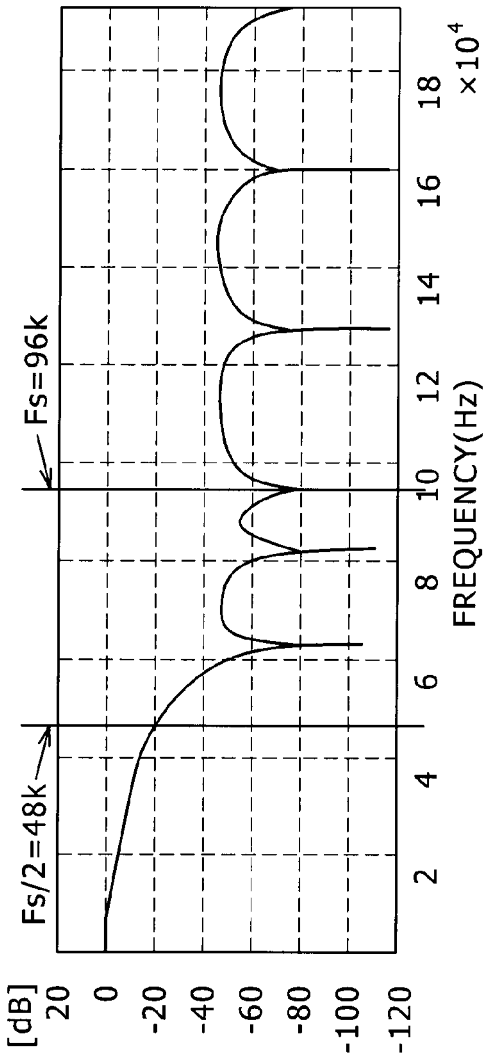

For example, it is assumed to use, as an example, an FIR Hamming filter having a Hamming window of a filter length of 768 samples (256×3) in a sampling frequency region of 256 Fs as seen in FIG. 14A. Frequency amplitude characteristics of the FIR Hamming filter of FIG. 14A are illustrated in FIGS. 14B and 14C. In this instance, since the filter length is 768 samples on 256 Fs as seen in FIG. 14A, the delay time on 256 Fs corresponds to 384 samples. Accordingly, the delay time on Fs (96 kHz) corresponds to 1.5 samples.

Figure 15A:
FIGS. 15A, 15B and 15C are a block diagram and diagrams illustrating a frequency amplitude characteristic where FIR hamming filters are two.
Figure 15B:
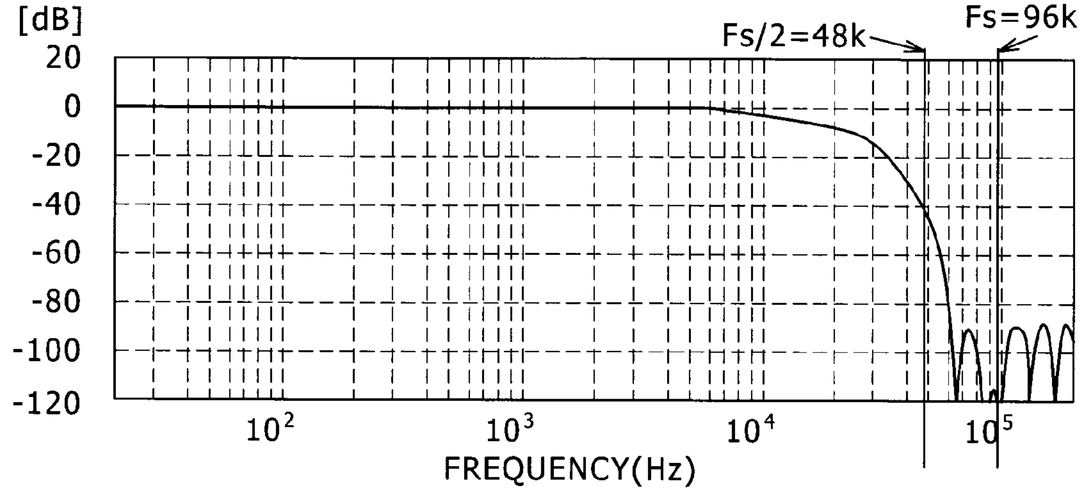
Figure 15C:
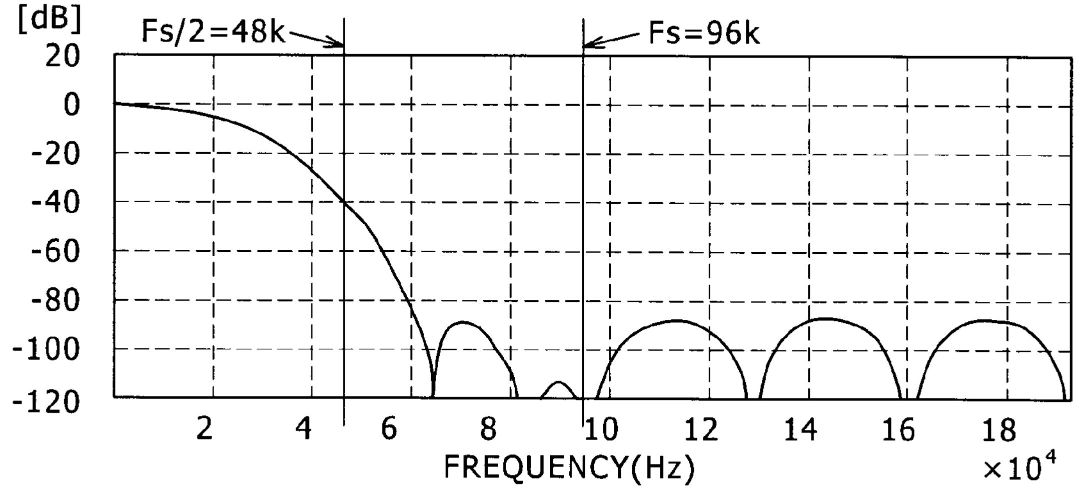

Meanwhile, FIGS. 15B and 15C illustrate frequency amplitudes where an FIR Hamming filter shown in FIG. 14A is connected at two stages in series as seen in FIG. 15A. The delay time in this instance is same as that in the case of FIGS. 13A to 13C and corresponds to 3 samples at Fs (96 kHz). While the delay amount is substantially same, where the characteristics illustrated in FIGS. 14B, 14C and 15B, 15C are compared with those illustrated in FIGS. 12B, 12C and 13B, 13C, although the attenuation amounts in the proximity of Fs/2 are low, those in the proximity of Fs are characteristically higher in the cases of FIGS. 14A, 14B and 15A, 15B than in the cases of FIGS. 12A, 12B and 13A, 13B.

In this manner, it can be recognized that, even if a filter having a great order number is not used, a desired attenuation characteristic can be obtained by increasing the number of filter stages or by using a filter which allows weighting while a linear phase characteristic is maintained.

Application of a Filter having a Low Order Number to a Noise Canceling Filter

Now, application of an ADC and a DAC which contain such a digital filter as described hereinabove to an actual noise canceling headphone system which uses digital signal processing is studied.

Housing Characteristic of a Headphone

First, since, as a significant presupposition, the present invention is directed principally to application of a headphone system, noise insulation by a housing characteristic of a headphone is studied first.

Figure 16:
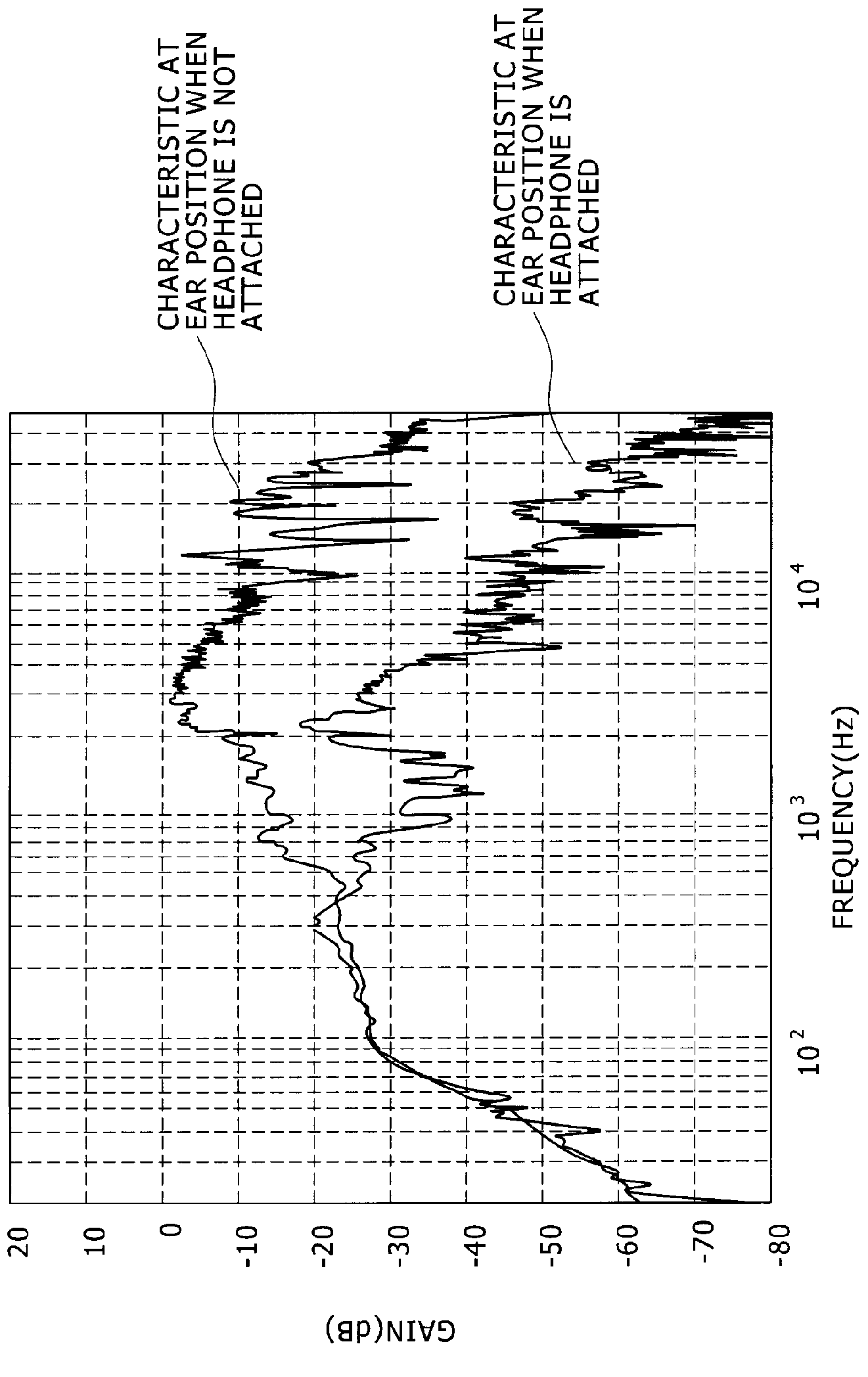
FIG. 16 is a diagram illustrating an example of characteristics of sound insulation of a general closed headphone.

FIG. 16 illustrates an example of noise insulation of a popular closed (not open) type headphone. In particular, FIG. 16 illustrates a result when white noise is reproduced from a speaker in an anechoic chamber and sound is collected by a dummy head spaced by 1 m from the speaker. In FIG. 16, the axis of abscissa indicates the frequency (Hz) and the axis of ordinate indicates the gain (dB). The gain on the axis of ordinate represents a relative value of the sound pressure. In FIG. 16, a characteristic at the near position where the headphone is not attached and a characteristic where the headphone is attached to the head are illustrated.

As can be seen from the characteristics illustrated in FIG. 16, although the sound insulation performance by the headphone housing is not exhibited very much in a low frequency region, a passive sound insulation performance of 20 dB to 30 dB or more is exhibited in a high frequency region of several hundreds Hz or more and the sound insulation performance increases as the frequency increases.

Digital Filter (β Circuit) 122

Now, attention is paid to the DSP/CPU section (β Circuit) 122 which is formed from a DSP or a CPU in a noise canceling system of the feedback type. Basically, the noise canceling system of the feedback type achieves noise attenuation by adding characteristics of the DSP/CPU section 122 (β Circuit) to such ADHM characteristics as seen in FIGS. 9A and 9B to arrange such a shape (characteristic) as seen in FIG. 4 to form a servo system.

Further, as described hereinabove, in an actual system which includes an ADC or a DAC, phase rotation occurs because delay by a digital filter circuit occurs without fail as seen in FIG. 6*c*. This makes one of causes which narrow the reduction effect region in FIG. 4, that is, a region indicated by slanting lines in FIG. 4.

In FIG. 9B, if attention is paid to the transition of the phase characteristic and the phase margin is estimated to be approximately 60 degrees, then the phase varies between approximately 120 degrees and −120 degrees while the frequency varies from 10 Hz to 4 kHz. If it is assumed that ideally the delay of the DSP/CPU section 122 is close to zero, then it can be recognized here that the range from a low frequency portion to approximately 4 kHz is an effective frequency band within which an attenuation effect can be expected with an actual feedback system.

It is to be that the frequency band higher than 4 kHz is a region within which a sufficient passive attenuation characteristic can be obtained by a headphone housing as seen from FIG. 16. Further, since some sound in a middle and high frequency regions is frequently used as a warning signal for the notification of danger or the like in a general life, it is necessary to take it into consideration that the noise canceling system does not attenuate the sound intentionally.

Putting the foregoing together, a high frequency limit of an effective frequency band of a noise canceling system is set, as an example, to 4 kHz from a systematic region or a range of application. It is to be noted that the effective frequency band up to 4 kHz is a frequency band within which an ideal DSP/CPU section 122 (β Circuit), that is, a DSP/CPU section 122 having a delay proximate to zero, can be applied. Actually, the effective frequency band is narrowed by phase rotation by delay, a characteristic of each transducer and so forth.

Delay of an ADC and a DAC and a passive sound insulation characteristic of a headphone housing are described above. Particularly while digital filters included in an ADC and a DAC are treated in FIGS. 12*a* to 15*c*, the digital filters are designed intentionally as "comparatively low-order filters" in order to make the delay time short in the Fs (in the examples described, 96 kHz) sampling region. Actually, where the digital filters described are used in an ADC or a DAC used for a sound content of a comparatively wide band handled in a CD, an SACD (Super Audio Compact Disk) or a DVD (Digital Versatile Disk), the attenuation amount of them is small and is not very much preferable.

However, if the nature that the object of reduction is noise (hereinafter described) principally in a low frequency region, the passive characteristic of the headphone housing described hereinabove, a general property of a transducer existing in the system and so forth are taken into consideration, then the noise canceling system functions sufficiently even with the "comparatively low-order filter". This is provided below.

It is to be noted that, while the term "comparatively low-order" is used above, usually a linear phase FIR filter is used for processing in an oversampling region in the ADC 121 and the DAC 123 as described hereinabove, and although the representation of "low-order" is used, the low order here signifies that the filter length on the oversampled MFs region is at least greater than M samples.

Verification That Noise Cancellation Is Possible Using a Low-Order Filter

As the background to the fact that a low-order filter can be adopted sufficiently as a component of a noise canceling system even if it has an aliasing leakage characteristic as seen from FIGS. 12A to 15C, it is considered as an important factor that the frequency band of object noise is approximately 4 kHz and is very low in comparison with the sampling frequency Fs and that the frequency of Fs/2 exceeds the audible range (20 kHz). It is to be noted that, if the former is represented by the frequency band ratio, then it is as low as 1/20 or less at Fs of 96 kHz and 1/10 or less at Fs of 48 kHz. As the sampling frequency Fs increases, naturally this ratio increases.

Figure 17A:
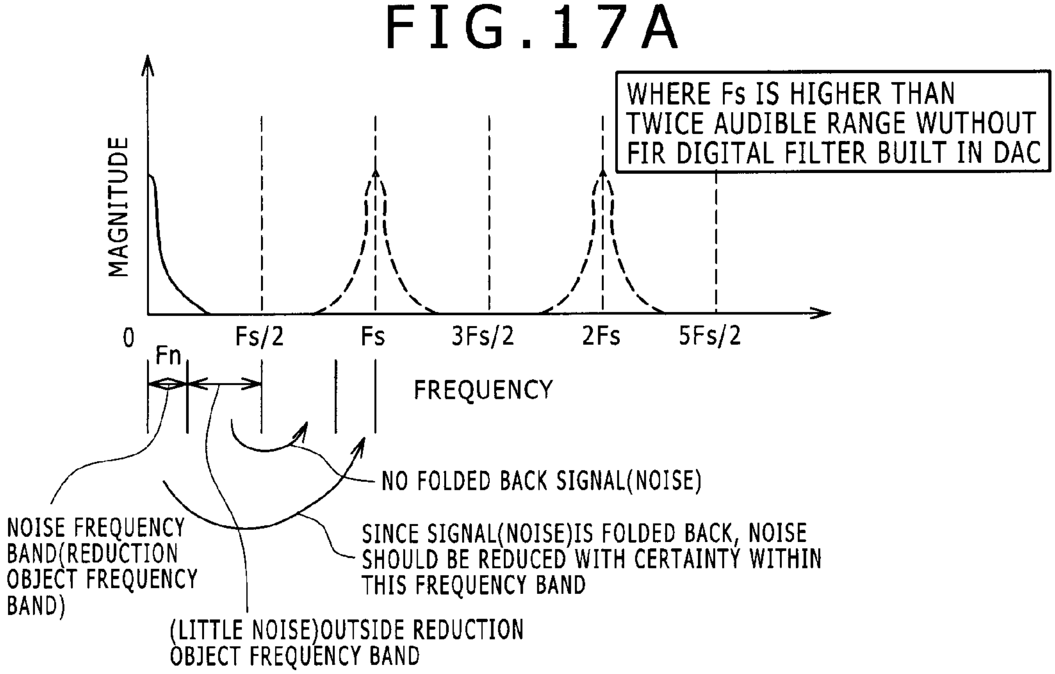
FIGS. 17A, 17B and 17C are graphs illustrating a characteristic of the DAC which is produced in different conditions.
Figure 17B:
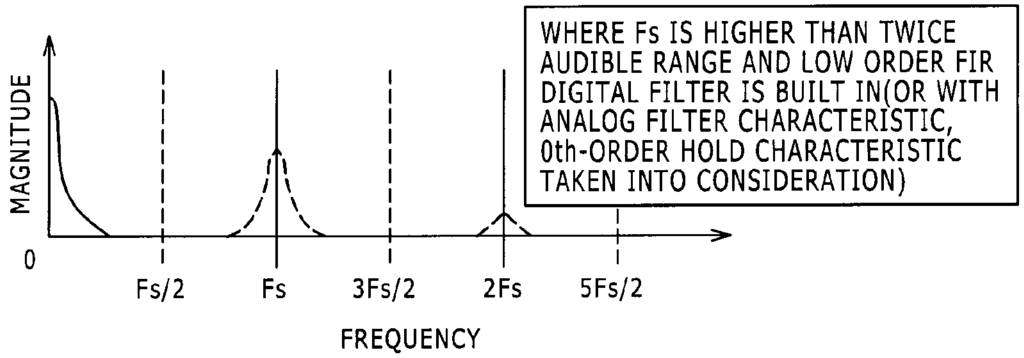
Figure 17C:
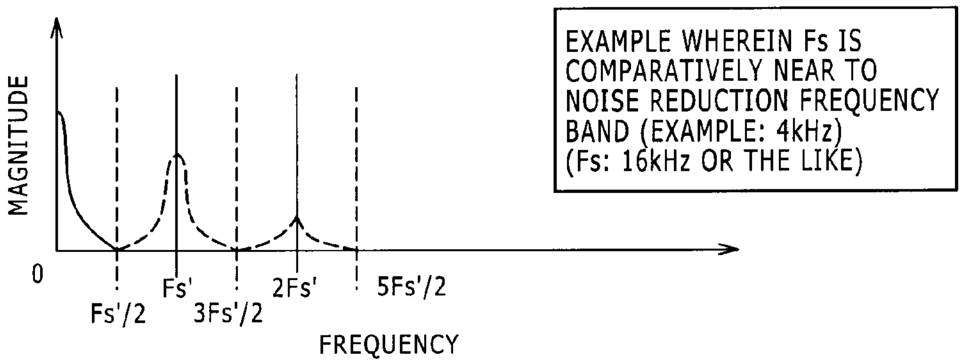

FIGS. 17A to 17C illustrate characteristics of DACs which are formed in different conditions. Here, in order to make the filter shape in the ADC and the DAC clear again, a state is considered wherein the noise reduction object bandwidth (noise reduction frequency band) is set to a frequency proximate to that of DC to Fn (Hz (here, Fn=4 kHz) and, as an easy example, the DAC 123 includes no FIR filter. In this instance, an imaging signal is generated in a frequency region higher than Fs/2 and a signal having such a frequency band characteristic as seen in FIG. 17A is outputted from the DAC 123.

Here, as regards the inside of the headphone, it is assumed that almost all noise components have a frequency lower than Fn (=4 kHz) because of a passive sound insulation characteristic and this frequency Fn has the highest frequency value of the noise reduction object. At this time, since noise signals of a frequency lower than Fn to Fs/2 little exist in the space, such an object which is to be folded back in a high frequency band as seen in FIG. 17A does not exist. Here, if it is assumed that the input sound section in FIG. 1 is not used or usually a sound signal lower than 3 kHz is used, then no unnecessary imaging signal is generated.

If such an imaging signal of a frequency higher than Fs/2 is not generated, then sound of a frequency higher than Fn little exists in the housing. Therefore, if a loop of the feedback type is considered, then also aliasing by the ADC after sound collected by the microphone does not occur in the frequency band. It is to be noted that, if Fs/2 is higher than the audible range, that is, if Fs is higher than twice the audible range, then even if imaging should appear, this is not heard by the user at all.

However, since the frequency region lower than Fn has a level of a noise signal, the DAC generates such an output as seen in FIG. 17A for frequency bands of (Fs−Fn) to (Fs+Fn) and (2 Fs−Fn) to (2 Fs+Fn). Therefore, it is originally necessary to sufficiently lower the level within the frequency band by FIR filtering.

Although the folding back noise successively appears up to a very high frequency band, basically it can be easily achieved to increase the attenuation as the frequency increases even with an ordinary low-order filter. Here, a characteristic of the DAC 123 where Fs is higher than twice the audible range and a low-order FIR filter is built in a DAC (or analog filter characteristic or a 0th-order holed characteristic is taken into consideration) is illustrated in FIG. 17B. As can be apparently seen from FIG. 17B, although the folding back noise successively appears up to a very high frequency region, basically the attenuation can be increased as the frequency increases even with an ordinary low-order filter.

Further, since also the aperture effect of the 0th-order hold characteristic of the analog filter or the DAC connected at a stage after the DAC attenuates by an increasing amount as the frequency increases although the attenuation is moderate, it is natural to consider that it has such a characteristic as seen in FIG. 17B. Putting the foregoing together, it can be recognized that what is to care is the lowest imaging noise frequency band (Fs−Fn) to (Fs+Fn) in practical use.

It is possible to design the attenuation characteristic such that it is particularly good only within the frequency band while, in the other frequency band, the delay time takes precedence (the filter length is made shorter) such that some aliasing leakage gain may be permitted. For example, a filter having such frequency characteristics as seen in FIGS. 18A and 18B may be produced and incorporated as a filter built in a DAC.

Figure 18A:
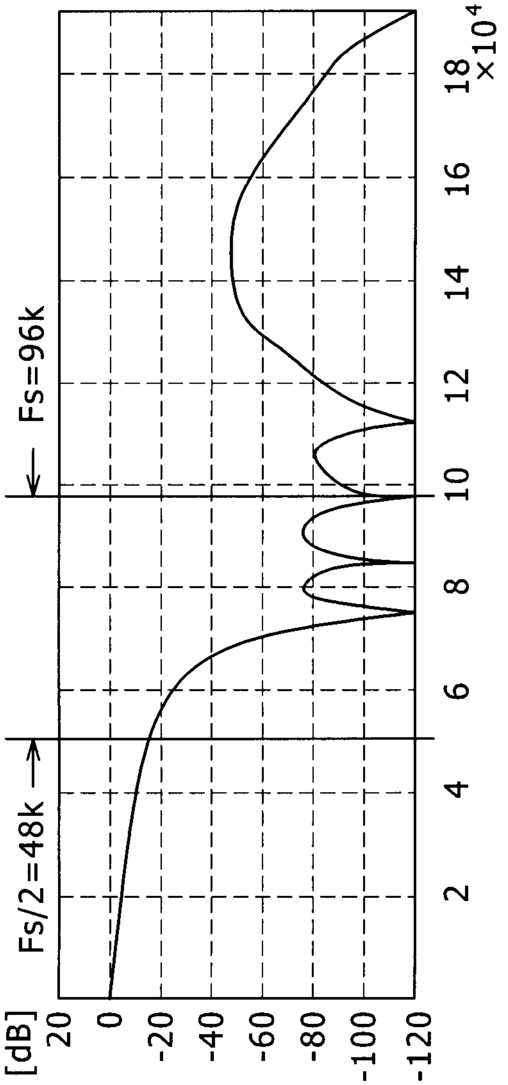
FIGS. 18A and 18B are diagrams illustrating frequency characteristics of target filters.
Figure 18B:
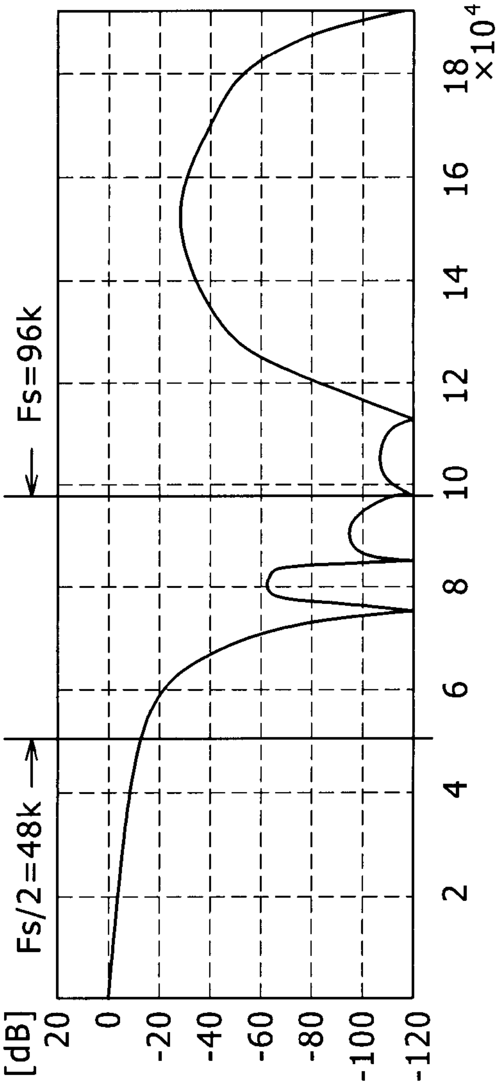

In particular, a filter may be produced wherein predetermined attenuation can be assured in the proximity of the sampling frequency Fs (=96 kHz) as seen in FIGS. 18A and 18B. More particularly, a filter may be used wherein attenuation by more than −60 dB can be assured within the range of (Fs−4 kHz) to (Fs+4 kHz) with reference to the sampling frequency Fs.

Further, as regards the sampling frequency Fs, since it is set such that Fs/2 is higher than the audible range so that leakage from the filter may not be heard as sound, even if a folded back signal exists, it is not heard as sound. Consequently, the hearing person does not feel an unfamiliar feeling.

Further, if the sampling frequency Fs is set to twice the audible range (more than 20 kHz), then since it is spaced sufficiently away from a level with which an actual example of a noise reduction object (4 kHz) is examined, also the position of a frequency of an object of folding back is far away from the noise reduction frequency band Fn. As a result, it is not necessary to demand the steepness for the low order FIR digital filter itself.

It is to be noted that, as seen from FIG. 17C which indicates a characteristic of the FB filter circuit 12 where the sampling frequency Fs is comparatively near to the noise reduction frequency band Fn (in the present example, 4 kHz) like a case wherein the sampling frequency Fs is, for example, 16 kHz, if the sampling frequency Fs is 16 kHz, then a steep filter which has sufficient attenuation in 12 kHz to 20 kHz may be required. This leads to increase of the order number (number of filter taps) and increase of the delay amount.

Further, while the description above relates to an example of the DAC, this similarly applies also to the ADC if the substance of an analog output is rewritten with regard to an analog input. Therefore, it is possible to incorporate a similar filter shape using a filter having a built-in ADC to decrease the delay mount thereby to expand the effective frequency band of the noise canceling system.

Further, though not shown, where the sampling frequency Fs is Fs=96 kHz, if a cutoff portion is set to a frequency region in the proximity of 20 kHz which is a limit to the audible range or to an object frequency band (4 kHz) rather than to set a cutoff portion of an LPF, for example, at Fs/2 from a sampling theory making use of the audible range or a noise reduction object width and a start of an attenuation curve of an LPF is set to the point of the thus set cutoff portion, then even if the curve is moderate at 96 kHz of the sampling frequency Fs, sufficient attenuation can be anticipated.

From the foregoing, as a digital filter (low order FIR filter) to be used in the ADC 121 and the DAC 123, a digital filter should be used which has such a characteristic that a desired attenuation amount is obtained in the proximity of the sampling frequency Fs and, more particularly, attenuation of −60 dB or more can be assured over a region of approximately (Fs−4 kHz) to (Fs+4 kHz) with regard to the sampling frequency Fs.

Further, a filter may be used wherein an aliasing leakage component in the other frequency regions than the frequency region of approximately (Fs−4 kHz) to (Fs+4 kHz) given above is accepted to suppress group delay of the digital filter which arises in a processing mechanism in the inside of a conversion processing device 1, lower than 1 ms. Further, if the sampling frequency Fs is set to a frequency higher than twice (approximately 40 kHz) the audible range, then even if filter delay exists, this is not heard as audible sound.

If a filter having such characteristics as described above is used, then an existing sigma-delta (Σ-Δ) type filter can be used without using an expensive ADC or DAC which can perform high speed conversion, and this does not increase the production cost of the FB filter circuit 12.

Influence of a Low Order Filter on a Noise Canceling System

In the following, an influence where a filter with which a desired attenuation amount is obtained only within a predetermined range in the proximity of a sampling frequency as described above is used in one or both of the ADC 121 and the DAC 123 in the entire noise sampling system which includes the ADC 121 and the DAC 123 is studied.

Figure 19:
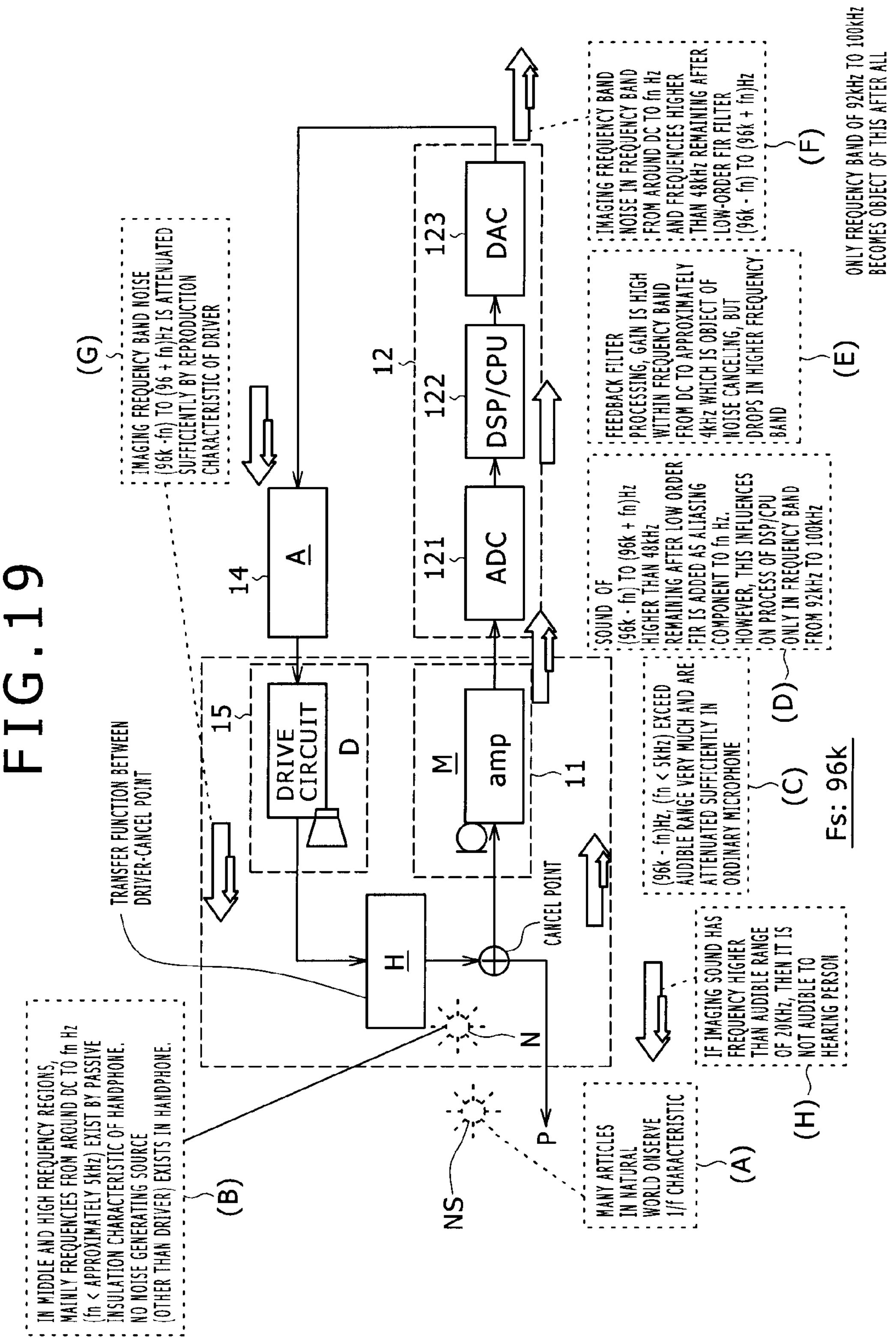
FIG. 19 is a block diagram illustrating a configuration of and a state of signals in a noise canceling system which operates with a sampling frequency of 96 kHz.

FIG. 19 illustrates a configuration of the noise canceling system which includes the ADC 121, DAC 123 and DSP/CPU section 122 and operates with the sampling frequency Fs=96 kHz and states of signals in the noise canceling system. Meanwhile, FIG. 20 illustrates behaviors and responses at two frequencies of 500 Hz and 5 kHz as particular examples relating to a filter (low order FIR filter) used in the ADC 121 and the DAC 123 of the FB filter circuit 12 of the noise canceling system shown in FIG. 19. Supplementary description to the substance relating to the "low order FIR filter" and aliasing described hereinabove is given below with reference to FIGS. 19 and 20.

First, it is known that noise of an object of reduction handled in a noise canceling headphone has a sound pressure characteristic of a shape proximate to approximately 1/f principally in a natural environment (except an artificial sound environment ((A) in FIG. 19), and the noise has a noise characteristic that it increases as the frequency decreases. Therefore, where the noise characteristics of 500 Hz and 5 kHz are compared with each other, it can be expected that the noise in the proximity of 5 kHz is lower by approximately 20 dB then the noise in the proximity of 500 Hz ((A) of FIG. 20).

Then, the noise in the natural environment undergoes a passive sound insulation effect by the headphone housing when it reaches the ear. It has been described with reference to FIGS. 14A to 15C that also the sound insulation characteristic thereof attenuates as the frequency increases. In other words, originally sound in a high frequency region is less likely to be generated and is less likely to enter the headphone housing due to the sound insulation property of the headphone. Therefore, almost nothing in the inside of the headphone naturally generates sound in a high frequency region ((B) of FIG. 19 and (B) of FIG. 20). It is to be noted that signal reproduction by the driver hereinafter described is no natural generation.

Noise (principally low-pitched sound) reduced passively by the headphone housing is collected by the microphone of the microphone and microphone amplification section 11 and enters the ADC 121 of the FB filter circuit 12 through the microphone amplifier. Although the microphone and microphone amplification section 11 is formed such that it has a flat characteristic within the audible range, there is no problem even if the characteristic in a high frequency region is reduced intentionally ((C) of FIG. 19 and (C) of FIG. 20). Meanwhile, outside the audible range, the gain characteristic is frequently reduced for the circuit protection, and it can be recognized also here that the high frequency characteristic higher than the audible range decreases as a passing point of a signal in the system.

Meanwhile, the ADC 121 of the FB filter circuit 12 is influenced by the low-order FIR filter. For example, at the sampling frequency Fs=96 kHz as seen in FIGS. 18A and 18B, if the aliasing filter is not insufficient, then where the analog signal inputted to the ADC 121 includes frequency components of 95.5 kHz, 96.5 kHz, 191.5 kHz, 192.5 kHz, . . . , those components which may not be removed by the filter are folded back and interpreted as components of 500 Hz. Consequently, actually a wrong signal is provided to the DSP/CPU section 122 which performs signal processing at a stage following the ADC 121 ((D) of FIG. 19 and (D) of FIG. 20). Similarly, where 91 kHz, 101 kHz, 187 kHz, 197 kHz, are included, they are interpreted as components of 5 kHz ((D) of FIG. 19 and (D) of FIG. 20).

However, that sound of a frequency higher than 90 kHz enters the system is considered to be less likely to occur upon generation of noise described above even if the passive sound insulation characteristic of the headphone is taken into consideration. Thus, it can be interpreted that a malfunction and a control error by the system by an influence of aliasing are less likely to occur. Thus, since, in FIG. 19, the first behavior in an aliasing/imaging frequency band which occurs in the proximity of the sampling frequency Fs is significant similarly as described above, a frequency higher than this frequency band is not mentioned any more.

In the DSP/CPU section 122, a filtering process of the high frequency region attenuation type is performed ((E) of FIG. 19 and (E) of FIG. 20). Also from the DAC 123 side after the digital filter processing by the DSP/CPU section 122, a component which has not been removed by the filter remains as an image component and is emitted as sound to the outside of the DAC 123.

Also here, if the attenuation of the components of 500 Hz by the filter is insufficient, then components of 95.5 kHz, 96.5 kHz, 191.5 kHz, 192.5 kHz, are generated depending upon the remaining components, and the components of 5 kHz are outputted as components of 91 kHz, 101 kHz, 187 kHz, 197 kHz, ((F) of FIG. 19 and (F) of FIG. 20). Naturally, if some filtering is applied, then usually a higher frequency component exhibits increased attenuation ((G) of FIG. 20).

Further, even if such components as mentioned above are outputted from a reproduction driver, they have frequencies higher than the audible range and may not be heard by a hearing person ((G) of FIG. 19). A signal outputted from the DAC 123 and including such unnecessary imaging components is emitted as sound into the space by the amplifier 14 and the driver 15. However, if an actual driver does not have a reproduction frequency band which extends to a frequency band higher than the audible range, then it may not reproduce such a very high frequency region naturally. Consequently, the imaging components are not reproduced into the space ((H) of FIG. 20). Further, if the imaging sound has a frequency higher than the audible range of 20 kHz, then it may not be heard by the hearing person.

Accordingly, where the low order FIR filter described hereinabove is used in the ADC 121 or the DAC 123, even if aliasing leakage occurs, no problem occurs with the feedback system used for cancellation of the noise, but the feedback system operates normally similarly as in the case wherein an ordinary high order FIR filter is used.

Figure 21:
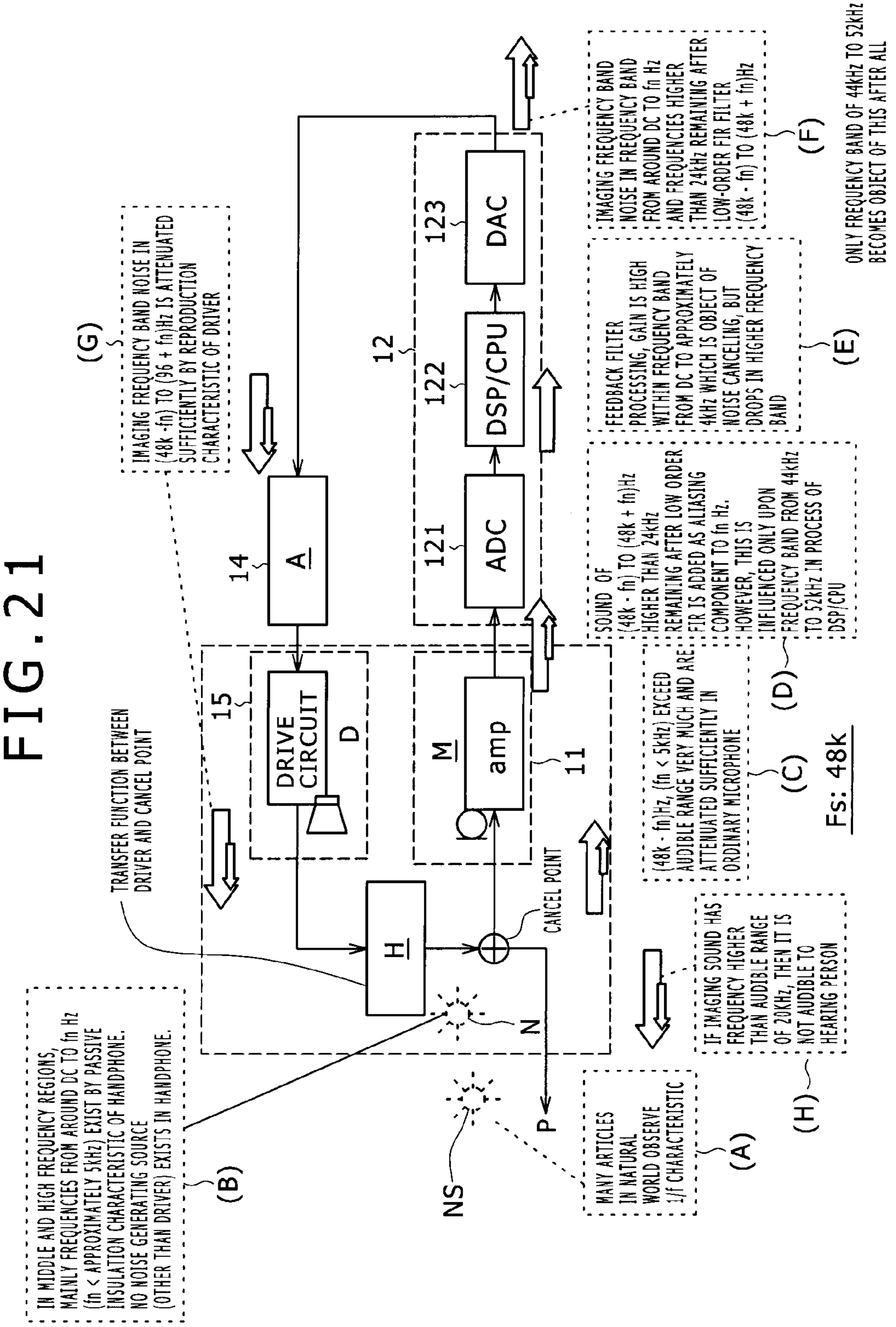
FIG. 21 is a block diagram illustrating a configuration of and a state of signals in a noise canceling system which operates with a sampling frequency of 48 kHz.

It is to be noted that a configuration of a noise canceling system which includes an ADC, a DAC and a DSP/CPU and operates with the sampling frequency Fs=48 kHz and states of signals in the noise canceling system are illustrated in FIG. 21. Further, behaviors and responses at two frequencies of 500 Hz and 5 kHz as particular examples relating to filters used in the ADC and the DAC of the noise canceling system shown in FIG. 21 are illustrated in FIG. 22. As can be seen apparently from FIGS. 21 and 22, even where the sampling frequency Fs is Fs=48 kHz, there is no problem similarly as in the case wherein the sampling frequency Fs is Fs=96 kHz described hereinabove with reference to FIGS. 19 and 20.

Particularly in the case of the noise canceling system of the present embodiment, since the object of noise reduction ranges from a low frequency region to approximately 4 kHz as described hereinabove and sound of frequencies higher than 4 kHz does not exist in the headphone housing or is insulated sufficiently by the passive sound insulation, the sound is not an object of the active noise reduction.

It is to be noted that, while the foregoing description is given taking a case wherein the present invention is applied to a noise canceling system of the feedback type as an example, the present invention can be applied also to a noise canceling system of the feedforward type. In particular, replacement of the FF filter circuit (−α block circuit) 22 in such a digital system as described hereinabove with reference to FIGS. 6B and 6C is considered. Usually, a general ADC or DAC exhibits a great amount of phase rotation as seen from FIG. 7B.

In such a case that the phase rotation of F'ADHMα of the expression (2) in FIG. 5 become increases toward the high frequency band with respect to the phase rotation of the transfer function F (transfer function of the space) in FIG. 2B, it may be impossible to reduce noise in a continuous frequency region higher than the frequency band in whatever manner the internal digital filter of α is changed.

In particular, although the noise reduction effect remains where the phase difference between an actual noise waveform and a driver production signal waveform is within a range from −120 degrees to −240 degrees at the cancel point (ear position), noise increases if a phase difference occurs outside the range. Also in a frequency band higher than the frequency (240 degrees) at which the phases of the waveforms are separated from each other, it is possible to provide a gain of the transmission characteristic α. In this instance, however, when the transfer function F and F'ADHMα are compared with each other, although a noise reduction effect is obtained at or around a frequency at which the phases coincide with each other. However, in a frequency with which the phases do not coincide with each other or are reverse to each other, noise increases, resulting in failure in practical use.

Accordingly, a gain of the transfer characteristic a is normally provided within a low frequency region within which the degrees of phase rotation of them are not different from each very much. If the transfer function F has a greater amount of phase rotation than F'ADHMα, then since a delay component can be produced by the digital filter section α, noise reduction can be performed readily. From this, it can be anticipated to reduce the phase rotation of F'ADHMα to enhance the noise reduction effect by reducing the delay of the ADC and the DAC as in the case of the technique according to the present invention described hereinabove.

It is to be noted that, as regards noise entering from the outside, since it has high noise components in a low frequency region as described above, the problem of aliasing is less likely to occur, and the noise can be attenuated in advance using a characteristic of the microphone itself or the microphone amplifier. Further, even where the delay is 0.1 ms (millisecond), if the concept of the phase difference is adopted, then where a phase difference of −240 degrees (change by −60 degrees from −180 degrees) is considered, the limit to the effective frequency band in the feedforward system is approximately 1.67 kHz. However, depending upon the application, if control in a low frequency region, for example, lower than 100 Hz may be required, then a delay up to approximately 1 ms is permitted. It is to be noted that a delay of 1 ms corresponds to a delay of 48 samples at the sampling frequency Fs=48 kHz and to a delay of 96 samples at the sampling frequency Fs=96 kHz.

Summary

From the foregoing, in a noise canceling system intended principally for use with a headphone and a headset, the FB filter circuit 12 of the noise canceling system of the feedback type can be formed in digitalized formation by using a low order FIR filter which satisfies the conditions described below in regard to one or both of the analog-digital conversion processing apparatus (ADC and DAC) inserted in a feedback loop in the system in order to increase the attenuation amount and the attenuation frequency band for reducing noise.

In particular, as conditions for a digital filter (low order FIR filter) to be used in one or both of the ADC 121 and the DAC 123 of the FB filter circuit 12, a digital filter (A) which uses a sampling frequency Fs of more than twice the audible range (higher than approximately 40 kHz), (B) which uses the sigma-delta (Σ-Δ) method as a conversion method, (C) which assures, where the sampling frequency is represented by Fs, attenuation of more than −60 dB over a frequency bandwidth approximately from (Fs−4 kHz) to (Fs+4 kHz), and (D) which permits an aliasing leakage component regarding frequency bands other than the frequency band specified in the condition (C) above thereby to suppress a group delay of the digital filter, which is generated in a processing mechanism in the conversion processing apparatus, to 1 ms or less, should be used.

Figure 23:
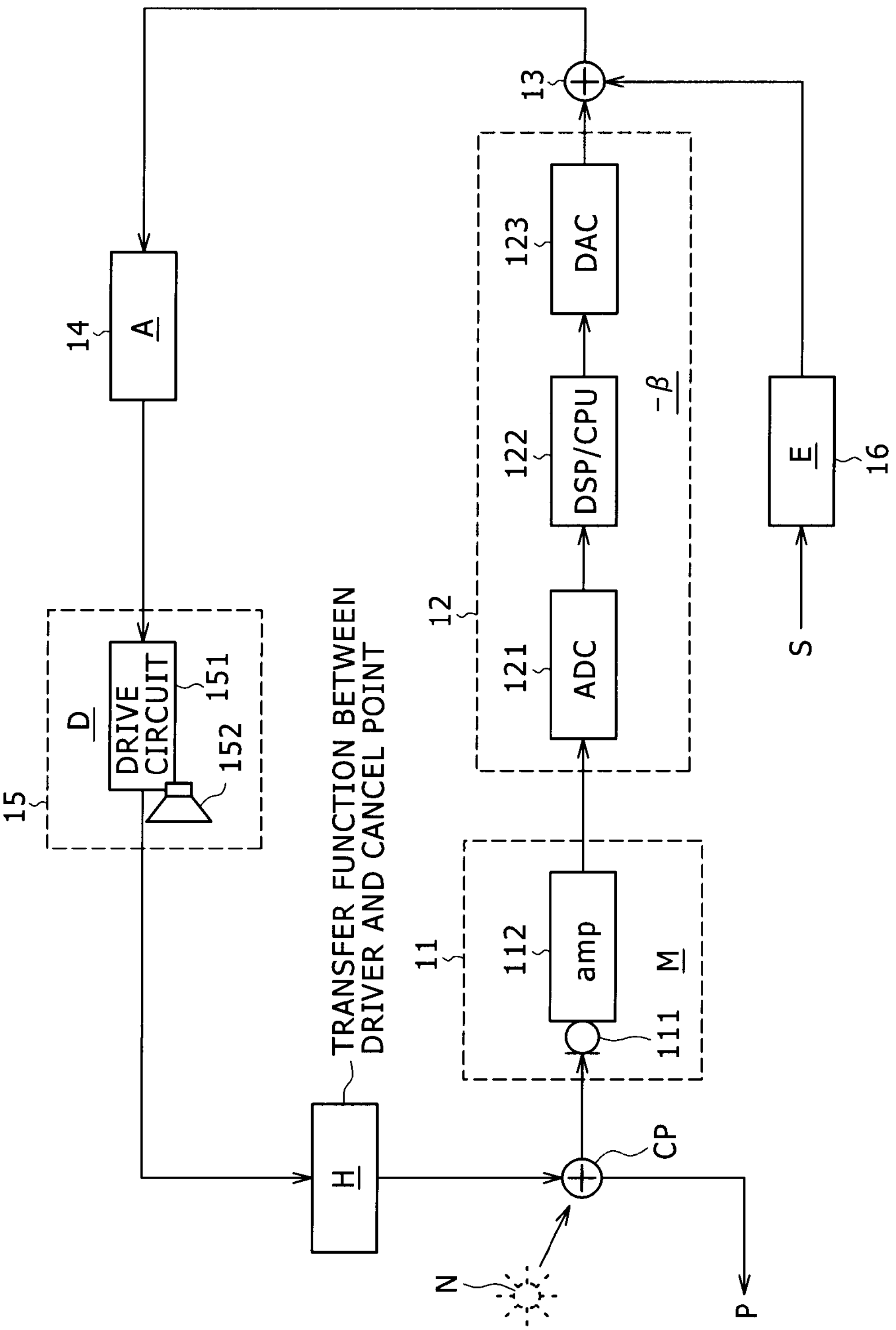
FIG. 23 is a block diagram showing a noise canceling system of the feedback type.

If the configuration for the condition is summarized, then a low order FIR filter used in one or both of the ADC 121 and the DAC 123 of the FB filter circuit 12 in the noise canceling system of the feedback type as seen in FIG. 23 should be configured so as to satisfy the conditions (A) to (D) given above.

Further, while the noise canceling system of the feedback type described hereinabove with reference to FIG. 1 or 23 includes an equalizer 16 and receives supply of a sound signal of an object of hearing from the outside such as a music reproduction apparatus or a microphone, according to the present invention, the application thereof is not limited to this. For example, the present invention can be applied also to a noise canceling system of the feedback type which is formed for reduction of noise and does not receive supply of a sound signal of an object of hearing from the outside such as a music reproduction apparatus or a microphone.

It is to be noted that, as described hereinabove, the feedback system achieves a noise reduction effect by processing a sound signal collected by the microphone attached in the inside of the housing of a headphone or a headset and reproducing the sound signal by means of a driver in the inside of the headphone so as to form a servo mechanism.

Further, principally in a noise canceling system whose noise reduction object is a headphone or a headset, if a low order FIR filter which satisfies the conditions specified below is used for one or both of the analog and digital conversion processing apparatus (ADC and DAC) inserted in the feedforward block in the system in order to increase the attenuation amount and the attenuation frequency band by and in which noise is to be reduced, then the FF filter circuit 22 of a noise canceling system of the feedforward type can be formed in digitalized formation.

As conditions for a digital filter (low order FIR filter) to be used in one or both of the ADC 221 and the DAC 223 of the FF filter circuit 22, a digital filter (A) which uses a sampling frequency Fs of more than twice the audible range (higher than approximately 40 kHz), (B) which uses the sigma-delta (Σ-Δ) method as a conversion method, (C) which assures, where the sampling frequency is represented by Fs, attenuation of more than −60 dB over a frequency band approximately from (Fs−4 kHz) to (Fs+4 kHz), and (D) which permits an aliasing leakage component regarding frequency bands other than the frequency band specified in the condition (C) above thereby to suppress the group delay of the digital filter, which is generated in a processing mechanism in the conversion processing apparatus, to 1 ms or less, should be used.

Figure 24:
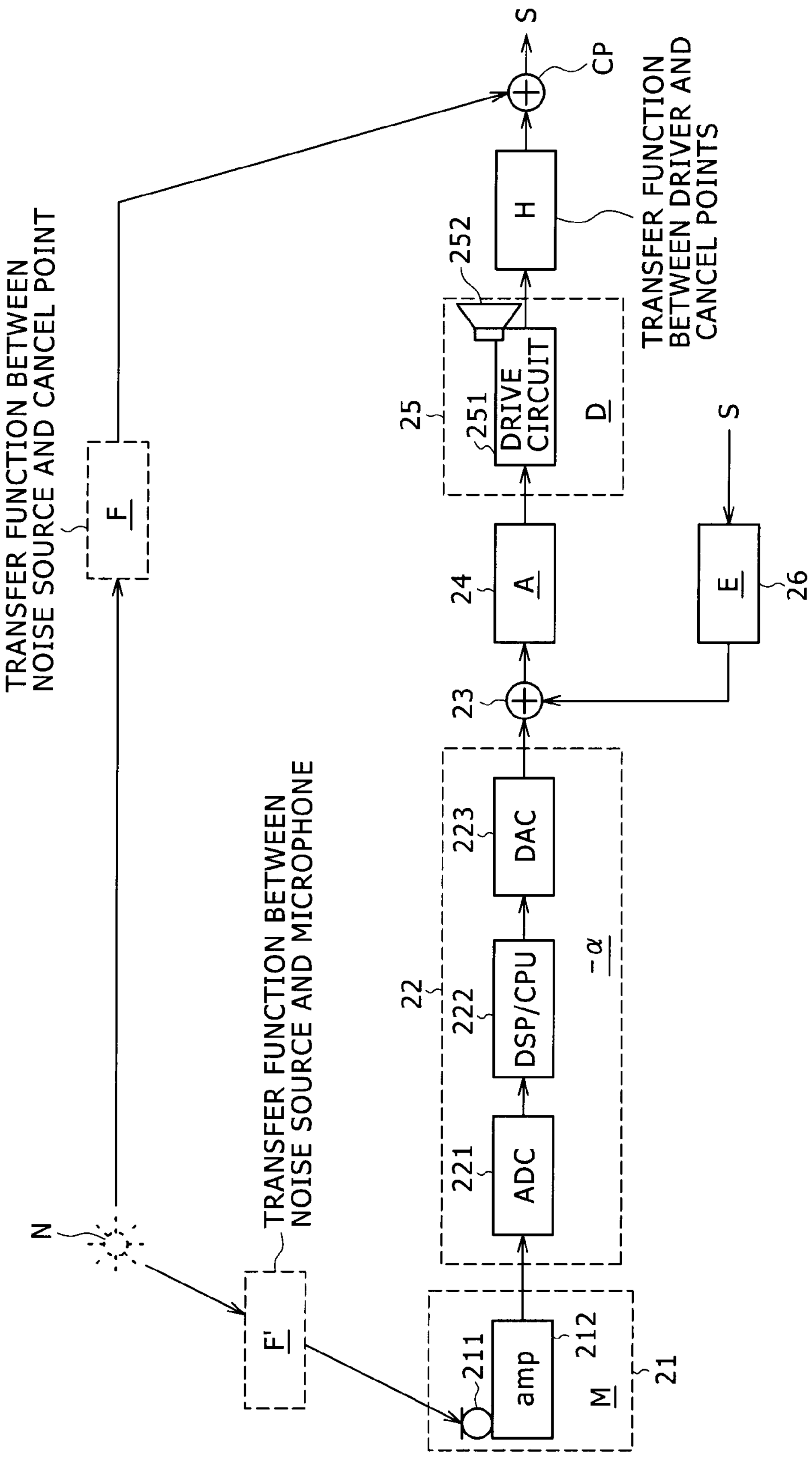
FIG. 24 is a block diagram showing a noise canceling system of the feedforward type.

If the configuration for the conditions is summarized, then a low order FIR filter used in one or both of the ADC 221 and the DAC 223 of the FF filter circuit 22 in the noise canceling system of the feedforward type as seen in FIG. 24 should be configured so as to satisfy the conditions (A) to (D) given above.

Further, the noise canceling system of the feedback type can be configured such that it includes an equalizer 26 and receives supply of a sound signal of an object of hearing from the outside such as a music reproduction apparatus or a microphone. Further, for example, the present invention can be applied also to a noise canceling system of the feedforward type which is formed for reduction of noise and does not receive supply of a sound signal of an object of hearing from the outside such as a music reproduction apparatus or a microphone.

It is to be noted that the feedforward system is configured such that, as described hereinabove, the sound signal collected by the microphone attached to the outer side of the housing of a headphone or a headset is processed and then reproduced by means of the driver in the headphone to achieve a noise reduction effect.

Digital Filter Circuit by Software

The components of the FB filter circuit 12 shown in FIG. 10B except the non-aliasing filter 1211 and the low-pass filter 1233 which process an analog signal can be implemented also by a program executed by a DSP or a CPU.

In particular, a DSP or a CPU which forms, for example, an FB filter circuit of a noise canceling system is configured such that it executes (1) an analog/digital conversion step of converting a noise signal collected by a microphone into a digital signal, (2) a first digital filter step of performing a decimation process of the digital noise signal converted into the digital signal at the analog/digital conversion step, (3) an arithmetic operation processing step of forming a digital noise reduction signal from the digital noise signal obtained by the decimation process at the first digital filter step, (4) a second digital filter step of performing an interpolation process of the digital noise reduction signal formed at the arithmetic operation processing step, and (5) a digital/analog conversion step of converting the digital noise reduction signal obtained by the interpolation process at the second digital filter step into an analog signal.

Then, at one or both of the first and second digital steps described above, a desired attenuation amount is obtained only within a predetermined range in the proximity of a sampling frequency around the sampling frequency. Consequently, the digital filter circuit according to the present embodiment can be implemented by a DSP and a CPU and software which is executed by the DSP and the CPU.

It is to be noted that, while also the description here is given taking a case wherein the FB filter circuit 12 of the noise canceling system of the feedback type is formed by software as an example, according to the present embodiment, the formation of the FB filter circuit 12 is not limited to this. Also the FF filter circuit 22 of the noise canceling system of the feedforward type can be implemented similarly by a program which is executed by a DSP or a CPU.

Then, also where the FB filter circuit 12 of the noise canceling system of the feedback type or the FF filter circuit 23 of the noise canceling system of the feedforward type is configured from software, it should be configured particularly so as to satisfy conditions (A) that it uses a sampling frequency Fs of more than twice (approximately 40 kHz) the audible range, (B) that it uses the sigma-delta (Σ-Δ) method as a conversion method, (C) that it assures, where the sampling frequency is represented by Fs, attenuation of more than −60 dB over a frequency bandwidth approximately from (Fs−4 kHz) to (Fs+4 kHz), and (D) that it permits an aliasing leakage component regarding frequency bands other than the frequency band specified in the condition (C) above thereby to suppress a group delay of the digital filter, which is generated in a processing mechanism in the conversion processing apparatus, to 1 ms or less.

Others

Figure 25:
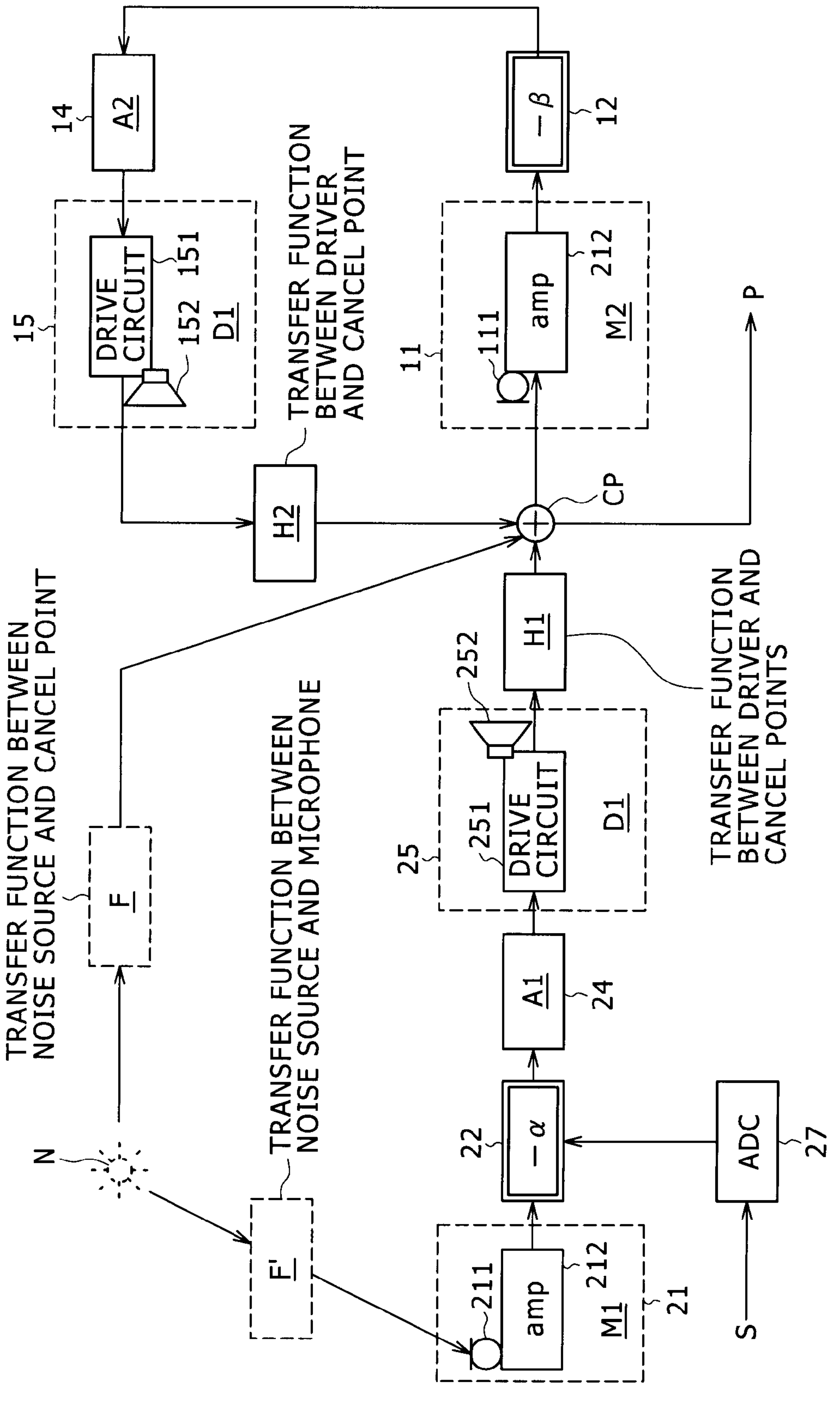
FIGS. 25 and 26 are block diagrams showing different examples of a configuration of a noise canceling system which includes both of the feedback system and the feedforward system.
Figure 26:
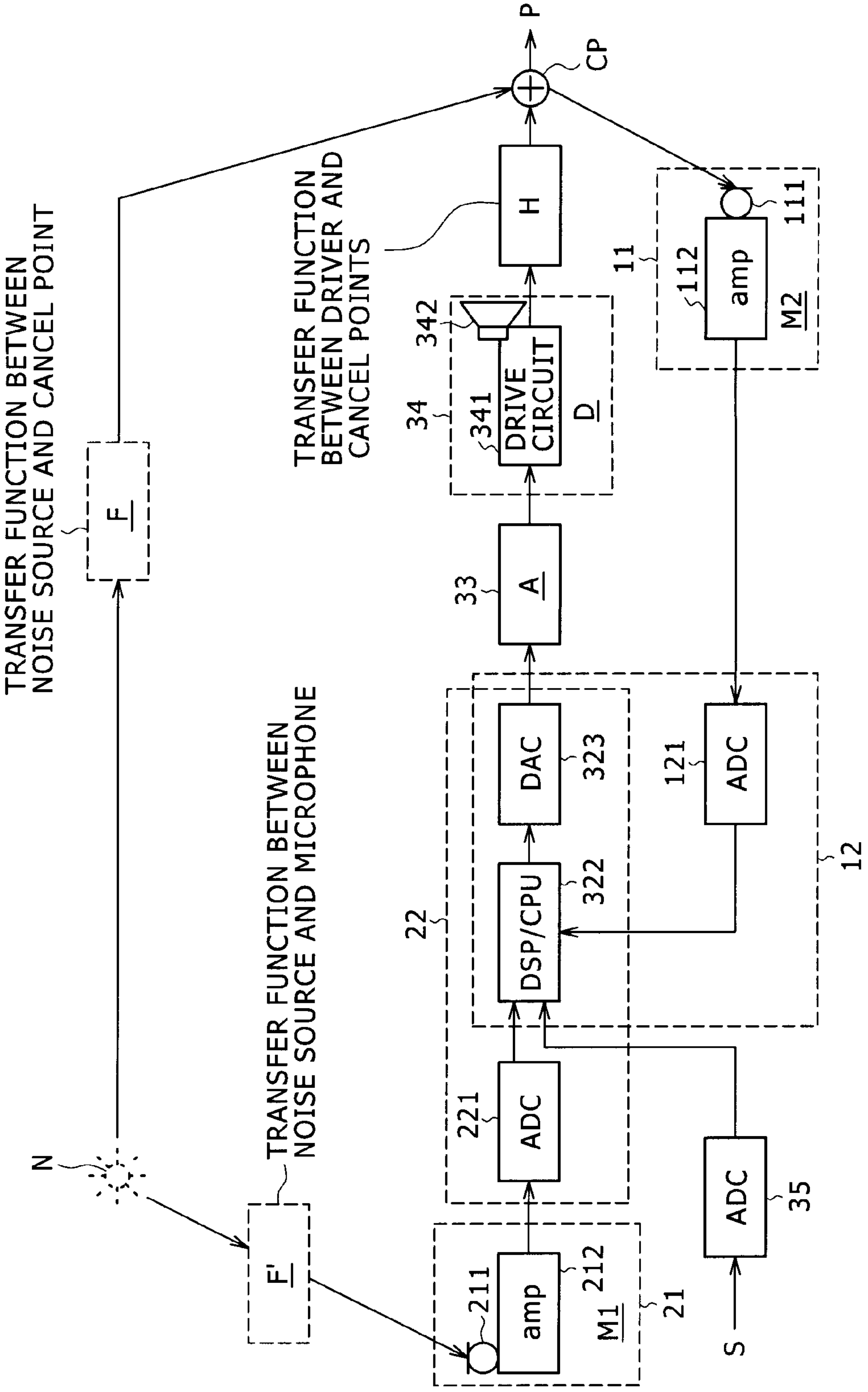

The present invention allows simultaneous application of the feedback system and the feedforward system to a noise canceling system in which the feedback system and the feedforward system are applied simultaneously as in a noise canceling system shown in FIG. 25 or 26.

Referring to FIG. 25, the noise canceling system shown includes a noise canceling system section of the feedforward type which includes a microphone and microphone amplification section 21, an FF filter circuit 22, a power amplifier 24 and a driver 25 and involves a transfer function Hi between the driver and the cancel point, another transfer function F between the noise source and the cancel point, and a transfer function F' between the noise source and the microphone. The noise canceling system further includes a noise canceling system section of the feedback type which includes a microphone and microphone amplification section 11, an FB filter circuit 12, a power amplifier 14 and a driver 15 and involves a transfer function H2 between the driver and the cancel point.

The FB filter circuit 12 includes an ADC 121, a DSP/CPU section 122 and a DAC 123 similarly to the FB filter circuit 12 shown in FIG. 23. A low order FIR filter which satisfies the conditions (A) to (D) described hereinabove can be used as a digital filter which is used in one or both of the ADC 121 and the DAC 123.

Meanwhile, the FF filter circuit 22 includes an ADC 221, a DSP/CPU section 222 and a DAC 223 similarly to the FF filter circuit 22 shown in FIG. 24. A low order FIR filter which satisfies the conditions (A) to (D) described hereinabove is used as a digital filter which is used in one or both of the ADC 221 and the DAC 223.

It is to be noted that, while, in FIG. 25, a sound signal (input sound) S from the outside is supplied to the FF filter circuit 22 after it is converted into a digital signal by an ADC 27, the digitized sound signal of the input sound S is supplied to the DSP/CPU section 222 of the FF filter circuit 22, by which it is synthesized with the sound signal from the microphone and microphone amplification section 21.

In this manner, since the two power amplifiers 14 and 24 and the two drivers 15 and 25 are provided in the headphone housing, the noise canceling system shown in FIG. 25 is configured so as to include both of noise canceling systems of the feedback type and the feedforward type. Consequently, advantages of the two systems can be utilized simultaneously.

Meanwhile, FIG. 26 shows a noise canceling system which involves both of the feedback system and the feedforward system similarly as in the noise canceling system of FIG. 25. Referring to FIG. 26, in the noise canceling system shown, the two power amplifiers 14 and 24 in FIG. 25 are unified into a single power amplifier 33, and the two drivers 15 and 25 are unified into a single driver 34. Further, a DSP/CPU section 322 and a DAC 323 are used commonly between the FB filter circuit 12 and the FF filter circuit 22 while separate ADCs are used in the FB filter circuit 12 and the FF filter circuit 22. Then, a signal of the feedback system and a signal of the feedforward system are added by the DSP/CPU section 322.

Also in the noise canceling system shown in FIG. 26, a low order FIR filter which satisfies the conditions (A) to (D) described hereinabove is used as a digital filter which is used in one or more of the ADC 121, ADC 221 and DAC 323.

In this manner, also the noise canceling system shown in FIG. 26 is configured so as to have both of noise canceling systems of the feedback type and the feedforward type but in a simplified form. Consequently, the advantages of the two systems can be utilized simultaneously.

In this manner, also in a noise canceling system which includes a noise canceling system of the feedforward type and a noise canceling system of the feedback type, if a digital filter of an ADC or a DAC used in an FB filter circuit or an FF filter circuit is formed from a low order FIR filter which satisfies the conditions (A) to (D) described hereinabove, then digitalized formation of the FB filter circuit or the FF filter circuit can be implemented at a low cost.

It is to be noted that, in the embodiment described hereinabove, a digital filter which can assure a predetermined attenuation amount (more than −60 dB) within a predetermined range (−4 kHz≦Fs≦4 kHz) around the sampling frequency Fs described hereinabove is used in both of the decimation filter 1213 and the interpolation filter 1231 of the FB filter circuit 12 shown in FIG. 10.

However, according to the present embodiment, the use of a digital filter is not limited to this. Where the processing capacity of one or both of the decimation filter 1213 and the interpolation filter 1231 is improved without any increase of the cost or in a like case, a digital filter which can assure a predetermined attenuation amount (more than −60 dB) within a predetermined range (−4 kHz≦Fs≦4 kHz) around the sampling frequency Fs may be used in at least one of the decimation filter 1213 and the interpolation filter 1231.

Further, as described hereinabove, the present invention can be applied also to a noise canceling system for a headphone system for enjoying sound of reproduced music and can be applied naturally also to a noise canceling system for a headset which is used in a case wherein a user works at a place filled with very high noise such as in a factory or on an airport for reducing noise. Furthermore, if the present invention is applied to a portable telephone set, then telephone conversation with clear sound can be anticipated also under noise. In other words, the present invention can be applied also to a portable telephone set.

It should be understood by those skilled in the art that various modifications, combinations, sub-combinations and alterations may occur depending on design requirements and other factors insofar as they are within the scope of the appended claims or the equivalents thereof.

What is claimed is:

1. A digital filter circuit for producing a noise reduction signal for reducing noise based on a noise signal outputted from a microphone which collects the noise, comprising:

an analog/digital conversion section configured to convert the noise signal into a digital noise signal;

a first digital filter section configured to decimate the digital noise signal to generate a decimated digital noise signal;

an arithmetic operation processing section configured to produce a digital noise reduction signal based on the decimated digital noise signal;

a second digital filter section configured to interpolate the digital noise reduction signal to generate an interpolated digital noise reduction signal; and a digital/analog conversion section configured to convert the interpolated digital noise reduction signal into an analog signal, wherein said first digital filter section and/or said second digital filter section are configured to obtain a predetermined attenuation amount within a predetermined range in a proximity of a sampling frequency around the sampling frequency, the sampling frequency is a frequency higher than twice an audible range, the predetermined range in the proximity of the sampling frequency is within a range from −4 kHz to +4 kHz around the sampling frequency, and said predetermined attenuation amount is more than −60 dB.

2. The digital filter circuit according to claim 1, wherein said analog/digital conversion section and said digital/analog conversion section are sigma-delta conversion sections.

3. The digital filter circuit according to claim 1, wherein said arithmetic operation processing section produces the digital noise reduction signal for feedback control.

4. The digital filter circuit according to claim 1, wherein said arithmetic operation processing section produces the digital noise reduction signal for feedforward control.

5. The digital filter circuit according to claim 1, wherein the first and second digital filters include a plurality of equal stages to obtain the predetermined attenuation amount.

6. A digital filter method, comprising:

converting a noise signal outputted from a microphone, which collects noise, into a digital noise signal;

decimating the digital noise signal to generate a decimated digital noise signal;

producing a digital noise reduction signal based on the decimated digital noise signal;

interpolating the digital noise reduction signal to generate an interpolated digital noise signal; and converting the interpolated digital noise reduction signal into an analog signal, wherein at the decimation and/or the interpolation, a predetermined attenuation amount is obtained within a predetermined range in the proximity of a sampling frequency around the sampling frequency, the sampling frequency is a frequency higher than twice an audible range, the predetermined range in the proximity of the sampling frequency is within a range from −4 kHz to +4 kHz around the sampling frequency, and said predetermined attenuation amount is more than −60 dB.

7. The digital filter method according to claim 6, wherein, the analog/digital conversion and the digital/analog conversion, are performed using sigma-delta conversion.

8. The digital filter method according to claim 6, wherein, at the arithmetic operation processing, a digital noise reduction signal for feedback control is produced.

9. The digital filter method according to claim 6, wherein, at the arithmetic operation processing, a digital noise reduction signal for feedforward control is produced.

10. A non-transitory computer-readable recording medium storing computer-readable instructions thereon that when executed by a computer cause the computer to perform a method comprising:

converting a noise signal outputted from a microphone, which collects noise, into a digital noise signal;

decimating the digital noise signal to generate a decimated digital noise signal;

producing a digital noise reduction signal based on the decimated digital noise signal;

interpolating the digital noise reduction signal to generate an interpolated digital noise signal; and converting the interpolated digital noise reduction signal into an analog signal, wherein at the decimation and/or the interpolation, a predetermined attenuation amount is obtained within a predetermined range in the proximity of a sampling frequency around the sampling frequency the sampling frequency is a frequency higher than twice an audible range, the predetermined range in the proximity of the sampling frequency is within a range from −4 kHz to +4 kHz around the sampling frequency, and said predetermined attenuation amount is more than −60 dB.

11. A noise canceling system of the feedback type, comprising:

a microphone provided on a housing to be attached to an ear portion of a user and configured to collect noise and output a noise signal;

a digital filter circuit including an analog/digital conversion section configured to convert the noise signal into a digital noise signal, a first digital filter section configured to decimate the digital noise signal to generate a decimated digital noise signal, an arithmetic operation processing section configured to produce a digital noise reduction signal based on the decimated digital noise signal, a second digital filter section configured to interpolate the digital noise reduction signal to generate an interpolated digital noise reduction signal, and a digital/analog conversion section configured to convert the interpolated digital noise reduction signal into an analog signal; and a driver configured to emit noise reproduction sound based on the analog signal;

wherein said first digital filter section and/or said second digital filter section are configured to obtain a predetermined attenuation amount within a predetermined range in the proximity of a sampling frequency around the sampling frequency, the sampling frequency is a frequency higher than twice an audible range, the predetermined range in the proximity of the sampling frequency is within a range from −4 kHz to +4 kHz around the sampling frequency, and said predetermined attenuation amount is more than −60 dB.

12. The noise canceling system according to claim 11, wherein said analog/digital conversion section and said digital/analog conversion section are sigma-delta conversion sections.

13. A noise canceling system of the feedforward type, comprising:

a microphone provided on a housing to be attached to an ear portion of a user and configured to collect noise and output a noise signal;

a digital filter circuit including an analog/digital conversion section configured to convert the noise signal into a digital noise signal, a first digital filter section configured to decimate the digital noise signal to generate a decimated digital noise signal, an arithmetic operation processing section configured to produce a digital noise reduction signal based on the decimated digital noise signal, a second digital filter section configured to interpolate the digital noise reduction signal to generate an interpolated digital noise reduction signal, and a digital/analog conversion section configured to convert the interpolated digital noise reduction signal into an analog signal; and a driver configured to emit noise reproduction sound based on the analog signal;

wherein said first digital filter section and/or said second digital filter section are configured to obtain a predetermined attenuation amount within a predetermined range in the proximity of a sampling frequency around the sampling frequency, the sampling frequency is a frequency higher than twice an audible range, the predetermined range in the proximity of the sampling frequency is within a range from −4 kHz to +4 kHz around the sampling frequency, and said predetermined attenuation amount is more than −60 dB.

14. The noise canceling system according to claim 13, wherein said analog/digital conversion section and said digital/analog conversion section are sigma-delta conversion sections.

* * * * *